United States Patent
Albrecht et al.

(10) Patent No.: US 10,226,589 B2
(45) Date of Patent: *Mar. 12, 2019

(54) INSUFFLATING OPTICAL SURGICAL INSTRUMENT

(71) Applicant: APPLIED MEDICAL RESOURCES CORPORATION, Rancho Santa Margarita, CA (US)

(72) Inventors: Jeremy J. Albrecht, Rancho Santa Margarita, CA (US); John R. Brustad, Rancho Santa Margarita, CA (US); Scott V. Taylor, Rancho Santa Margarita, CA (US); Gary M. Johnson, Rancho Santa Margarita, CA (US); Nabil Hilal, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 515 days.

This patent is subject to a terminal disclaimer.

(21) Appl. No.: 14/841,941

(22) Filed: Sep. 1, 2015

(65) Prior Publication Data

US 2015/0367088 A1 Dec. 24, 2015

Related U.S. Application Data

(63) Continuation of application No. 13/356,260, filed on Jan. 23, 2012, now Pat. No. 9,155,558, which is a
(Continued)

(51) Int. Cl.
*A61M 13/00* (2006.01)
*A61B 17/34* (2006.01)
(Continued)

(52) U.S. Cl.
CPC ....... *A61M 13/003* (2013.01); *A61B 17/3417* (2013.01); *A61B 17/3462* (2013.01);
(Continued)

(58) Field of Classification Search
CPC ................ A61M 13/00; A61M 13/003; A61M 2202/0007; A61M 2202/02;
(Continued)

(56) References Cited

U.S. PATENT DOCUMENTS

| RE682 E | 4/1859 | Peale |
|---|---|---|
| 184,573 A | 11/1876 | Becker |

(Continued)

FOREIGN PATENT DOCUMENTS

| BE | 1 006 811 A6 | 12/1994 |
|---|---|---|
| DE | 0365049 C | 12/1922 |

(Continued)

OTHER PUBLICATIONS

U.S. Appl. No. 10/745,262, filed Dec. 23, 2003; Title: "Catheter With Conduit Traversing Tip" (abandoned).
(Continued)

*Primary Examiner* — Imani Hayman
(74) *Attorney, Agent, or Firm* — Patrick Ikehara

(57) ABSTRACT

An insufflating surgical instrument adapted for movement across an abdominal wall to insufflate an abdominal region of a patient is disclosed. The instrument comprises a shaft having an insufflation channel extending between a proximal end and a distal end, the insufflation channel being adapted for connection to a source of fluid under pressure at the proximal end. A tip is at the distal end and a vent hole is formed in the tip being in connection with the insufflation channel and adapted to expel fluid under pressure to insufflate the abdominal region. The tip is formed of a transparent material to facilitate visualization of the abdominal wall and
(Continued)

region. The shaft includes a lumen extending along the axis between the proximal end and the distal end to enable insertion of a laparoscope. The lumen and insufflation channel may be formed as separate channels or as one shared channel.

19 Claims, 13 Drawing Sheets

Related U.S. Application Data continuation of application No. 12/766,118, filed on Apr. 23, 2010, now Pat. No. 8,128,590, which is a continuation of application No. 11/170,567, filed on Jun. 29, 2005, now Pat. No. 7,708,713, which is a continuation-in-part of application No. 10/956,167, filed on Oct. 1, 2004, now Pat. No. 7,947,058.

(60) Provisional application No. 60/584,302, filed on Jun. 29, 2004, provisional application No. 60/508,390, filed on Oct. 3, 2003.

(51) Int. Cl.
    *A61B 1/06* (2006.01)
    *A61B 90/00* (2016.01)

(52) U.S. Cl.
    CPC ............ *A61B 17/3474* (2013.01); *A61B 1/06* (2013.01); *A61B 17/3494* (2013.01); *A61B 90/361* (2016.02); *A61B 2017/346* (2013.01); *A61B 2017/349* (2013.01); *A61B 2017/3454* (2013.01); *A61M 2202/0007* (2013.01); *A61M 2202/02* (2013.01); *A61M 2202/0468* (2013.01); *A61M 2205/3337* (2013.01)

(58) Field of Classification Search
    CPC .. A61M 2202/0468; A61M 2205/3337; A61B 17/3474; A61B 90/361; A61B 17/3462; A61B 17/3494; A61B 1/06; A61B 2017/3454; A61B 2017/346; A61B 2017/349; A61B 17/3417
    See application file for complete search history.

(56) References Cited

U.S. PATENT DOCUMENTS

| | | |
|---|---|---|
| 207,932 A | 9/1878 | Alvord |
| 224,513 A | 2/1880 | Burdon |
| 396,754 A | 1/1889 | Mayfield |
| 764,322 A | 7/1904 | Wiegand |
| 1,147,408 A | 7/1915 | Kelis |
| 1,672,258 A | 6/1928 | Hippenmeyer |
| 1,727,495 A | 9/1929 | Wappler |
| 1,845,727 A | 2/1932 | Slaughter |
| 2,024,069 A | 12/1935 | Sharp |
| 2,102,274 A | 12/1937 | Larimore |
| 2,189,343 A | 2/1940 | Fritz |
| 2,301,338 A | 11/1942 | Smith |
| 2,434,594 A | 1/1948 | Schultz |
| 2,441,143 A | 5/1948 | Gracey |
| 2,646,701 A | 7/1953 | Lietin |
| 2,699,770 A | 1/1955 | Fourestier et al. |
| 2,764,148 A | 9/1956 | Sheldon |
| 2,764,149 A | 9/1956 | Sheldon |
| 2,769,355 A | 11/1956 | Henry |
| 2,877,368 A | 3/1959 | Sheldon |
| 2,932,294 A | 4/1960 | Fourestier et al. |
| 3,005,468 A | 10/1961 | Erwin et al. |
| 3,021,834 A | 2/1962 | Sheldon |
| 3,033,226 A | 5/1962 | Allen |
| 3,042,022 A | 7/1962 | Sheldon |
| 3,224,320 A | 12/1965 | Knudsen |
| 3,277,922 A | 10/1966 | Eisel |
| 3,279,460 A | 10/1966 | Sheldon |
| 3,357,433 A | 12/1967 | Fourestier et al. |
| 3,385,553 A | 5/1968 | Braun |
| 3,417,745 A | 12/1968 | Sheldon |
| 3,434,747 A | 4/1969 | Sheldon |
| 3,437,747 A | 4/1969 | Sheldon |
| 3,459,189 A | 8/1969 | Alley et al. |
| 3,556,085 A | 1/1971 | Takahashi |
| 3,613,684 A | 10/1971 | Sheridan |
| 3,653,338 A | 4/1972 | Sauey |
| 3,791,379 A | 2/1974 | Storz |
| 3,817,251 A | 6/1974 | Hasson |
| 3,821,956 A | 7/1974 | Gordhamer |
| 3,870,036 A | 3/1975 | Fiore |
| 3,961,621 A | 6/1976 | Northeved |
| 3,971,385 A | 7/1976 | Corbett |
| 3,994,287 A | 11/1976 | Turp |
| 3,994,301 A | 11/1976 | Agris |
| 4,028,987 A | 6/1977 | Wilson |
| 4,112,932 A | 9/1978 | Chiulli |
| 4,126,291 A | 11/1978 | Gilbert et al. |
| 4,150,929 A | 4/1979 | Brandt |
| 4,168,882 A | 9/1979 | Hopkins |
| 4,180,068 A | 12/1979 | Jacobsen et al. |
| 4,191,191 A | 3/1980 | Auburn |
| 4,222,375 A | 9/1980 | Martinez |
| 4,248,214 A | 2/1981 | Hannah et al. |
| 4,254,762 A | 3/1981 | Yoon |
| 4,269,192 A | 5/1981 | Matsuo |
| 4,274,771 A | 6/1981 | Nishimura |
| 4,285,618 A | 8/1981 | Shanley |
| 4,299,230 A | 11/1981 | Kubota |
| 4,311,138 A | 1/1982 | Sugarman |
| 4,319,563 A | 3/1982 | Kubota |
| 4,356,826 A | 11/1982 | Kubota |
| 4,386,179 A | 5/1983 | Sterling |
| 4,414,966 A | 11/1983 | Stednitz |
| 4,429,856 A | 2/1984 | Jackson |
| 4,436,519 A | 3/1984 | O'Neill |
| 4,493,444 A | 1/1985 | Deli et al. |
| 4,498,902 A | 2/1985 | Ash et al. |
| 4,524,805 A | 6/1985 | Hoffman |
| 4,535,773 A | 8/1985 | Yoon |
| 4,535,808 A | 8/1985 | Johanson et al. |
| 4,537,593 A | 8/1985 | Alchas |
| 4,567,882 A | 2/1986 | Heller |
| 4,601,710 A | 7/1986 | Moll |
| 4,607,619 A | 8/1986 | Seike et al. |
| 4,750,877 A | 6/1988 | McFarlane |
| 4,762,130 A | 8/1988 | Fogarty et al. |
| 4,779,613 A | 10/1988 | Hashiguchi et al. |
| 4,803,999 A | 2/1989 | Liegner |
| 4,813,400 A | 3/1989 | Washizuka et al. |
| 4,850,393 A | 7/1989 | Lashomb |
| 4,869,717 A | 9/1989 | Adair |
| 4,895,431 A | 1/1990 | Tsujluchi et al. |
| 4,901,142 A | 2/1990 | Ikuno et al. |
| 4,956,143 A | 9/1990 | McFarlane |
| 4,959,067 A | 9/1990 | Muller |
| 4,972,827 A | 11/1990 | Kishi et al. |
| 4,978,350 A | 12/1990 | Wagenknecht |
| 5,017,057 A | 5/1991 | Kruygor |
| 5,030,210 A | 7/1991 | Alchas |
| 5,041,100 A | 8/1991 | Rowland et al. |
| 5,057,082 A | 10/1991 | Burchette, Jr. |
| 5,066,288 A | 11/1991 | Deniego et al. |
| 5,098,379 A | 3/1992 | Conway |
| 5,098,388 A | 3/1992 | Kulkashi et al. |
| 5,104,316 A | 4/1992 | McSpadden |
| 5,104,388 A | 4/1992 | Quackenbush |
| 5,104,389 A | 4/1992 | Deem et al. |
| 5,114,407 A | 5/1992 | Burbank |
| 5,116,547 A | 5/1992 | Tsukahara et al. |
| 5,144,942 A | 9/1992 | Decarie et al. |
| 5,147,376 A | 9/1992 | Pianetti |
| 5,159,920 A | 11/1992 | Condon et al. |
| 5,163,941 A | 11/1992 | Garth et al. |

(56) References Cited

U.S. PATENT DOCUMENTS

| | | |
|---|---|---|
| 5,178,186 A | 1/1993 | Levasseur |
| 5,186,972 A | 2/1993 | Williams et al. |
| 5,197,955 A | 3/1993 | Stephens et al. |
| 5,207,656 A | 5/1993 | Kranys |
| 5,217,441 A | 6/1993 | Shichman |
| 5,221,163 A | 6/1993 | Nishimura |
| 5,240,397 A | 8/1993 | Fay et al. |
| 5,246,425 A | 9/1993 | Hunsberger et al. |
| 5,250,068 A | 10/1993 | Ideguchi et al. |
| 5,256,149 A | 10/1993 | Banik et al. |
| 5,258,003 A | 11/1993 | Ciaglia |
| 5,269,316 A | 12/1993 | Spitainy |
| 5,271,380 A | 12/1993 | Riek et al. |
| 5,279,567 A | 1/1994 | Ciaglia et al. |
| 5,288,290 A | 2/1994 | Brody |
| 5,290,276 A | 3/1994 | Sewell |
| 5,290,585 A | 3/1994 | Elton |
| 5,300,033 A | 5/1994 | Miller |
| 5,334,150 A | 8/1994 | Kaali |
| 5,342,382 A | 8/1994 | Brinkerhoff |
| 5,350,364 A | 9/1994 | Stephens et al. |
| 5,366,446 A | 11/1994 | Tal et al. |
| 5,370,624 A | 12/1994 | Edwards et al. |
| 5,372,588 A | 12/1994 | Farley |
| 5,374,253 A | 12/1994 | Burns, Sr. et al. |
| 5,380,291 A | 1/1995 | Kaali |
| 5,387,197 A | 2/1995 | Smith |
| 5,389,077 A | 2/1995 | Melinyshin et al. |
| 5,391,153 A | 2/1995 | Haber et al. |
| 5,391,248 A | 2/1995 | Brain |
| 5,392,766 A | 2/1995 | Masterson et al. |
| 5,405,328 A | 4/1995 | Vidal et al. |
| 5,407,427 A | 4/1995 | Zhu et al. |
| 5,431,151 A | 7/1995 | Riek et al. |
| 5,441,041 A | 8/1995 | Sauer et al. |
| 5,443,484 A | 8/1995 | Kirsch et al. |
| 5,445,615 A | 8/1995 | Yoon et al. |
| 5,454,791 A | 10/1995 | Tovey et al. |
| 5,480,410 A | 1/1996 | Cuschieri et al. |
| 5,510,065 A | 4/1996 | McFarlane |
| 5,540,711 A | 7/1996 | Kieturakis et al. |
| 5,542,845 A | 8/1996 | Jenkins |
| 5,549,546 A | 8/1996 | Schneider et al. |
| 5,551,947 A | 9/1996 | Kaai |
| 5,562,696 A | 10/1996 | Nobles et al. |
| 5,569,291 A | 10/1996 | Privitera |
| 5,569,292 A | 10/1996 | Scwemberger et al. |
| 5,577,993 A | 11/1996 | Zhu et al. |
| 5,591,186 A | 1/1997 | Wurster et al. |
| 5,591,192 A | 1/1997 | Privitera et al. |
| 5,593,402 A | 1/1997 | Patrick |
| 5,603,720 A | 2/1997 | Kieturakis |
| 5,609,562 A | 3/1997 | Kaali |
| 5,609,604 A | 3/1997 | Schwemberger et al. |
| 5,613,954 A | 3/1997 | Nelson et al. |
| 5,622,462 A | 4/1997 | Gakhar et al. |
| 5,630,805 A | 5/1997 | Ternamian |
| 5,634,908 A | 6/1997 | Loomas |
| 5,658,236 A | 8/1997 | Sauer |
| 5,662,615 A | 9/1997 | Blake, III |
| 5,662,673 A | 9/1997 | Kieturakis |
| 5,676,611 A | 10/1997 | Foster |
| 5,685,820 A | 11/1997 | Riek et al. |
| 5,695,462 A | 12/1997 | Sutcu et al. |
| 5,697,947 A | 12/1997 | Wolf |
| 5,720,730 A | 2/1998 | Blake, III |
| 5,720,761 A | 2/1998 | Kaali |
| 5,735,867 A | 4/1998 | Golser et al. |
| 5,738,628 A | 4/1998 | Sierocuk |
| 5,743,881 A | 4/1998 | Demco |
| 5,746,734 A | 5/1998 | Domandy, Jr. et al. |
| 5,752,970 A | 5/1998 | Yoon et al. |
| 5,759,185 A | 6/1998 | Grinberg |
| 5,779,697 A | 7/1998 | Glowa et al. |
| 5,779,967 A | 7/1998 | Hull |
| 5,785,693 A | 7/1998 | Halninig |
| 5,792,112 A | 8/1998 | Hart et al. |
| 5,797,888 A | 8/1998 | Yoon et al. |
| 5,797,944 A | 8/1998 | Nobeles et al. |
| 5,817,061 A | 10/1998 | Goodwin et al. |
| 5,817,062 A | 10/1998 | Flom et al. |
| 5,836,957 A | 11/1998 | Shulz |
| 5,842,971 A | 12/1998 | Yoon |
| 5,860,996 A | 1/1999 | Urban et al. |
| 5,865,809 A | 2/1999 | Moenning et al. |
| 5,871,474 A | 2/1999 | Hermann et al. |
| 5,876,202 A | 3/1999 | Berlin |
| 5,882,340 A | 3/1999 | Yoon |
| 5,884,639 A | 3/1999 | Chen |
| 5,891,013 A | 4/1999 | Thompson |
| 5,893,865 A | 4/1999 | Swindle |
| 5,904,699 A | 5/1999 | Schwemberger et al. |
| 5,913,818 A | 6/1999 | Co et al. |
| 5,922,351 A | 7/1999 | Daher |
| 5,924,452 A | 7/1999 | Szpapa et al. |
| 5,941,852 A | 8/1999 | Dunlap et al. |
| 5,957,884 A | 9/1999 | Hooven |
| 5,957,888 A | 9/1999 | Hinchliffe |
| 5,968,060 A | 10/1999 | Kellogg |
| 5,976,079 A | 11/1999 | Volz et al. |
| 5,976,168 A | 11/1999 | Chin |
| 5,980,809 A | 11/1999 | Crain et al. |
| 5,984,941 A | 11/1999 | Wilson |
| 6,001,084 A | 12/1999 | Riek |
| 6,007,481 A | 12/1999 | Riek et al. |
| 6,007,544 A | 12/1999 | Kim |
| 6,019,776 A | 2/2000 | Preissman |
| 6,024,551 A | 2/2000 | Yamaguchi |
| 6,030,406 A | 2/2000 | Davis |
| 6,043,310 A | 3/2000 | Liu et al. |
| 6,053,194 A | 4/2000 | Nelson et al. |
| 6,068,637 A | 5/2000 | Popov et al. |
| 6,077,481 A | 6/2000 | Ichida et al. |
| 6,092,551 A | 7/2000 | Bennett |
| 6,168,355 B1 | 1/2001 | Wardell |
| 6,179,528 B1 | 1/2001 | Wardell |
| 6,203,559 B1 | 3/2001 | Davis |
| 6,203,745 B1 | 3/2001 | Wachsmann et al. |
| 6,221,061 B1 | 4/2001 | Engelson et al. |
| 6,228,059 B1 | 5/2001 | Astarita |
| 6,228,063 B1 | 5/2001 | Aboul-Hosn |
| 6,270,484 B1 | 8/2001 | Yoon |
| 6,302,873 B1 | 10/2001 | Moenning |
| 6,319,266 B1 | 11/2001 | Stellon |
| 6,346,074 B1 | 2/2002 | Roth |
| 6,355,014 B1 | 3/2002 | Zadno-Azizi et al. |
| 6,387,043 B1 | 5/2002 | Yoon |
| 6,462,111 B1 | 10/2002 | Singh et al. |
| 6,468,228 B1 | 10/2002 | Topel et al. |
| 6,478,806 B2 | 11/2002 | McFarlane |
| 6,508,759 B1 | 1/2003 | Taylor et al. |
| 6,520,939 B2 | 2/2003 | Lafontaine |
| 6,579,298 B1 | 6/2003 | Bruneau et al. |
| 6,656,160 B1 | 12/2003 | Taylor et al. |
| 6,656,198 B2 | 12/2003 | Tsonton et al. |
| 6,685,630 B2 | 2/2004 | Sauer et al. |
| 6,764,107 B1 | 7/2004 | Obahi et al. |
| 6,770,731 B2 | 8/2004 | Mason et al. |
| 6,835,201 B2 | 12/2004 | O'Heeron |
| 6,884,253 B1 | 4/2005 | McFarlane |
| 6,887,194 B2 | 5/2005 | Hart et al. |
| 6,902,541 B2 | 6/2005 | McNally et al. |
| 6,939,296 B2 | 9/2005 | Ewers et al. |
| 7,008,979 B2 | 3/2006 | Schottman et al. |
| 7,037,303 B2 | 5/2006 | Beaufore et al. |
| 7,056,294 B2 | 6/2006 | Khairkhahan et al. |
| 7,056,329 B2 | 6/2006 | Kerr |
| 7,070,586 B2 | 7/2006 | Hart et al. |
| 7,182,752 B2 | 2/2007 | Stubbs |
| 7,344,519 B2 | 3/2008 | Wing et al. |
| 7,370,709 B2 | 5/2008 | Williamson, Jr. |
| 7,470,255 B2 | 12/2008 | Sterns et al. |
| 7,563,250 B2 | 7/2009 | Wenchell |
| 7,686,823 B2 | 3/2010 | Pingleton et al. |

(56) References Cited

U.S. PATENT DOCUMENTS

| | | |
|---|---|---|
| 7,708,713 B2 | 5/2010 | Albrecht et al. |
| 7,758,603 B2 | 7/2010 | Taylor et al. |
| 7,794,644 B2 | 9/2010 | Taylor et al. |
| 7,811,253 B2 | 10/2010 | Hart et al. |
| 7,942,862 B2 | 5/2011 | Hart et al. |
| 7,947,058 B2 | 5/2011 | Kahle et al. |
| 8,007,477 B2 | 8/2011 | Johnson et al. |
| 8,028,395 B2 | 10/2011 | Taylor et al. |
| 8,075,530 B2 | 12/2011 | Taylor et al. |
| 8,105,285 B2 | 1/2012 | Hart et al. |
| 8,128,590 B2 | 3/2012 | Albrecht et al. |
| 8,152,828 B2 | 4/2012 | Taylor et al. |
| 8,267,952 B2 | 9/2012 | Kahle et al. |
| 8,282,663 B2 | 10/2012 | Smith |
| 8,292,853 B2 | 10/2012 | Hart et al. |
| 8,317,815 B2 | 11/2012 | Mastri et al. |
| 8,377,090 B2 | 2/2013 | Taylor et al. |
| 8,382,663 B2 | 2/2013 | Taylor |
| 8,506,520 B2 | 8/2013 | Kahle et al. |
| 8,517,977 B2 | 8/2013 | Taylor et al. |
| 8,608,768 B2 | 12/2013 | Taylor et al. |
| 8,608,769 B2 | 12/2013 | Kahle et al. |
| 8,636,759 B2 | 1/2014 | Pingleton et al. |
| 8,961,493 B2 | 2/2015 | Hart et al. |
| 2002/0013597 A1 | 1/2002 | McFarlane |
| 2002/0026207 A1 | 2/2002 | Stellon et al. |
| 2002/0133188 A1 | 9/2002 | O'Heeron et al. |
| 2002/0183715 A1 | 12/2002 | Mantell et al. |
| 2002/0183775 A1 | 12/2002 | Tsonton et al. |
| 2003/0023201 A1 | 1/2003 | Aboul-Hosn |
| 2003/0032755 A1 | 2/2003 | Gomey et al. |
| 2003/0059263 A1 | 3/2003 | Chen |
| 2003/0187471 A1 | 10/2003 | Cooper |
| 2004/0015185 A1 | 1/2004 | Ewers et al. |
| 2004/0082969 A1 | 4/2004 | Kerr |
| 2004/0093000 A1 | 5/2004 | Kerr |
| 2004/0093018 A1 | 5/2004 | Johnson et al. |
| 2004/0106942 A1 | 6/2004 | Taylor et al. |
| 2004/0108623 A1 | 6/2004 | Deeter et al. |
| 2004/0167559 A1 | 8/2004 | Taylor et al. |
| 2004/0199127 A1 | 10/2004 | Jensen et al. |
| 2004/0204671 A1 | 10/2004 | Stubbs et al. |
| 2004/0230155 A1 | 11/2004 | Blanco et al. |
| 2004/0230217 A1 | 11/2004 | O'Heeron |
| 2004/0254517 A1 | 12/2004 | Quiroz-Mercado et al. |
| 2005/0033237 A1 | 2/2005 | Fentress et al. |
| 2005/0033246 A1 | 2/2005 | Ahlberg et al. |
| 2005/0038466 A1 | 2/2005 | O'Heeron et al. |
| 2005/0059865 A1 | 3/2005 | Kahle |
| 2005/0065543 A1 | 3/2005 | Kahle et al. |
| 2005/0107803 A1 | 5/2005 | Guanche |
| 2005/0107816 A1 | 5/2005 | Pingleton et al. |
| 2005/0113533 A1 | 5/2005 | Shaikh et al. |
| 2005/0149094 A1 | 7/2005 | Kashara et al. |
| 2005/0149096 A1 | 7/2005 | Hilal et al. |
| 2005/0159711 A1 | 7/2005 | Kathrani et al. |
| 2005/0216028 A1 | 9/2005 | Hart et al. |
| 2005/0227610 A1 | 10/2005 | Zukor et al. |
| 2005/0273133 A1 | 12/2005 | Schluzas et al. |
| 2005/0283122 A1 | 12/2005 | Nordgren |
| 2005/0288622 A1 | 12/2005 | Albrecht et al. |
| 2006/0030755 A1 | 2/2006 | Ewers et al. |
| 2006/0041270 A1 | 2/2006 | Lenker et al. |
| 2006/0030870 A1 | 3/2006 | Staudner |
| 2006/0047284 A1 | 3/2006 | Gresham |
| 2006/0058570 A1 | 3/2006 | Rapach et al. |
| 2006/0074374 A1 | 4/2006 | Gresham |
| 2006/0118189 A1 | 6/2006 | Trekulve et al. |
| 2006/0224174 A1 | 10/2006 | Smith et al. |
| 2006/0264991 A1 | 11/2006 | Johnson |
| 2007/0027453 A1 | 2/2007 | Hart et al. |
| 2007/0075465 A1 | 4/2007 | Taylor et al. |
| 2007/0088277 A1 | 4/2007 | McGinley |
| 2007/0239108 A1 | 10/2007 | Albrecht et al. |
| 2008/0065021 A1 | 3/2008 | Jenkins et al. |
| 2008/0086074 A1 | 4/2008 | Taylor et al. |
| 2008/0086093 A1 | 4/2008 | Steppe et al. |
| 2009/0030375 A1 | 1/2009 | Franer et al. |
| 2009/0137943 A1 | 5/2009 | Stearns et al. |
| 2009/0187079 A1 | 7/2009 | Albrecht et al. |
| 2009/0281500 A1 | 11/2009 | Acosta et al. |
| 2010/0025045 A1 | 2/2010 | Lake et al. |
| 2014/0114339 A1 | 4/2014 | Pingleton et al. |

FOREIGN PATENT DOCUMENTS

| | | |
|---|---|---|
| DE | 1616107 B1 | 4/1971 |
| DE | 2218901 A1 | 10/1973 |
| DE | 2538758 A1 | 3/1977 |
| DE | 2929233 A1 | 1/1980 |
| DE | 2922239 A1 | 12/1980 |
| DE | 4020956 A1 | 1/1991 |
| DE | 4133073 A1 | 4/1992 |
| DE | 4035146 A1 | 5/1992 |
| DE | 4116648 A1 | 11/1992 |
| DE | 29503750 U1 | 4/1995 |
| DE | 29521431 U1 | 4/1997 |
| DE | 19541041 | 5/1997 |
| DE | 19718086 A1 | 11/1998 |
| DE | 19819432 | 11/1999 |
| EP | 0135364 | 3/1985 |
| EP | 0312787 | 4/1989 |
| EP | 0347140 | 12/1989 |
| EP | 0369936 A1 | 5/1990 |
| EP | 0369937 A1 | 5/1990 |
| EP | 0474124 | 3/1992 |
| EP | 0548612 | 6/1993 |
| EP | 0556056 | 8/1993 |
| EP | 0664992 | 8/1995 |
| EP | 0724864 | 8/1996 |
| EP | 1074224 | 2/2001 |
| EP | 1582158 | 10/2005 |
| EP | 2229897 | 9/2010 |
| EP | 2233090 | 9/2010 |
| FR | 1370580 A | 8/1964 |
| GB | 2 124 970 | 2/1984 |
| GB | 186 005 | 9/1992 |
| GB | 2 313 316 | 11/1997 |
| JP | 408127661 | 5/1996 |
| JP | 09-173342 A | 7/1997 |
| JP | 2001-137253 | 5/2001 |
| SU | 0942730 A1 | 7/1982 |
| SU | 1328658 A1 | 8/1987 |
| SU | 1329769 A1 | 8/1987 |
| WO | WO 1993/25148 | 12/1993 |
| WO | WO 1994/11040 A1 | 5/1994 |
| WO | WO 96/01074 A2 | 1/1996 |
| WO | WO 1996/01132 | 1/1996 |
| WO | WO 1996/10361 | 4/1996 |
| WO | WO 1997/40758 | 11/1997 |
| WO | WO 1997/40758 A1 | 11/1997 |
| WO | WO 1998/33536 | 8/1998 |
| WO | WO 1999/02089 | 1/1999 |
| WO | WO 1999/15084 | 4/1999 |
| WO | WO 2000/018306 | 4/2000 |
| WO | WO 2000/054648 | 9/2000 |
| WO | WO 2001/01847 A1 | 1/2001 |
| WO | WO 2001/01871 A1 | 1/2001 |
| WO | WO 2001/008563 A2 | 2/2001 |
| WO | WO 2002/001998 | 1/2002 |
| WO | WO 2002/034108 | 5/2002 |
| WO | WO 2002/041795 A2 | 5/2002 |
| WO | WO 2003/026512 | 4/2003 |
| WO | WO 2003/032819 | 4/2003 |
| WO | WO 2003/096879 | 11/2003 |
| WO | WO 2004/037097 | 5/2004 |
| WO | WO 2004/093699 | 11/2004 |

(56) References Cited

FOREIGN PATENT DOCUMENTS

WO    WO 2005/063134    7/2005
WO    WO 2007/093957    8/2007

OTHER PUBLICATIONS

Co-Pending U.S. Appl. No. 11/549,872, filed Oct. 16, 2006, title: "Surgical Devices, Systems and Methods Thereof Having Gel Material, Gel Coatings, or Gel Lubricants".
Co-Pending U.S. Appl. No. 13/565,972, filed Aug. 3, 2012, title: "Bladeless Optical Obturator".
Co-Pending U.S. Appl. No. 13/356,260, filed Jan. 23, 2012, title: "Insufflating Optical Surgical Instrument".
Co-Pending U.S. Appl. No. 12/359,964, filed Jan. 26, 2009, title: "Insufflating Access System".
Co-Pending U.S. Appl. No. 13/462,330, filed May 2, 2012, title: "Low-Profile Surgical Universal Access Port".
International Bureau of WIPO, International Preliminary Report on Patentability for International Application No. PCT/US04/032346, dated May 20, 2008.
International Bureau of WIPO, International Preliminary Report on Patentability for International Application No. PCT/US2005/022716 dated Nov. 22, 2005.
International Bureau of WIPO, International Preliminary Report on Patentability for International Application No. PCT/US2006/060013, dated Apr. 24, 2008.
International Bureau of WIPO, The International Preliminary Report on Patentability for International Application No. PCT/US2009/058792, titled First Entry Trocar System, dated Mar. 29, 2011.
International Bureau of WIPO, The International Preliminary Report on Patentability for International Application No. PCT/US2007/080724, titled "Visual Insufflation Port", dated Apr. 7, 2009.
International Bureau of WIPO, The International Preliminary Report on Patentability for International Application No. PCT/US2009/32026, titled "Insufflating Access System", dated Jul. 27, 2010.
International Bureau of WIPO, The International Preliminary Report on Patentability for International Application No. PCT/US2004/000695, titled "Surgical Access Apparatus and Method", dated Jul. 22, 2005.
International Bureau of WIPO, The International Preliminary Report on Patentability for International Application No. PCT/US2004/04883, titled "Surgical Access Apparatus and Method", dated Sep. 9, 2005.
International Searching Authority, International Search Report and Written Opinion for International Application No. PCT/US2004/000695, titled "Surgical Access Apparatus and Method", dated Jan. 12, 2005.
International Searching Authority, International Search Report and Written Opinion for International Application No. PCT/US2004/04883, titled "Surgical Access Apparatus and Method", dated Mar. 31, 2005.
International Searching Authority, International Search Report and Written Opinion for International Application No. PCT/US2002/06759, titled "Bladeless Obturator", dated Jul. 12, 2002.
International Searching Authority, International Search Report and Written Opinion for International Application No. PCT/US2005/022716, titled "Insufflating Optical Surgical Instrument", dated Nov. 22, 2005.
European Patent Office, Supplementary European Search Report for European Patent Application No. EP 04 70 1731 based on International Application No. PCT/US2004/000695, titled "Surgical Access Apparatus and Method", dated Apr. 11, 2007.
European Patent Office, European Search Report for European Application No. 047017314, titled "Surgical Access Apparatus and Method", dated Mar. 30, 2007.
International Searching Authority, International Search Report and Written Opinion for International Application No. PCT/US2007/080724, titled "Visual Insufflation Port", dated Apr. 16, 2008.

European Patent Office, Supplementary European Search Report for European Patent Application No. EP 04712378, titled "Surgical Access Apparatus and Method", dated May 19, 2008.
International Searching Authority, International Search Report and Written Opinion for International Application No. PCT/US04/32346, titled Bladeless Optical Obturator, dated May 20, 2008.
European Patent Office, Supplementary European Search Report for European Patent Application No. EP 02706494.8, titled "Bladeless Obturator", dated Jun. 24, 2008.
European Patent Office, Supplementary European Search Report for European Patent Application No. EP 07843973.4, titled "Visual Insufflation Port" dated Oct. 4, 2008.
European Patent Office, Supplementary European Search Report for European Patent Application No. EP 03753017.7, titled "Blunt Tip Obturator", dated Nov. 21, 2008.
International Searching Authority, International Search Report and Written Opinion for International Application No. PCT/US2009/32026, titled "Insufflating Access System", dated Mar. 23, 2009.
International Searching Authority/US, International Search Report and The Written Opinion of the International Searching Authority dated May 27, 2009, for International Application No. PCT/US2009/037863, titled "Instrument Seal with Inverting Shroud", dated May 27, 2009.
The International Searching Authority, The International Search Report and The Written Opinion for International Application No. PCT/US2009/058792, titled "First Entry Trocar System", dated Dec. 23, 2009.
European Patent Office, Supplementary European Search Report for European Patent Application No. EP 04793965.7, titled "Bladeless Optical Obturator", dated Apr. 16, 2010.
European Patent Office, Supplementary European Search Report for European Patent Application No. EP 11154547.1, titled "Blunt Tip Obturator", dated Mar. 22, 2011.
European Patent Office, European Search Report for European Application No. 11191191.3, titled "Bladeless Obturator" dated Feb. 29, 2012.
European Patent Office, European Search Report for European Application No. 11191179.8, titled "Bladeless Obturator", dated Feb. 21, 2012.
European Patent Office, European Search Report for European Application No. 11191193.9, titled "Bladeless Obturator", dated Mar. 5, 2012.
European Patent Office, European Search Report for European Application No. 11191187.1, titled Bladeless Obturator, dated Feb. 23, 2012.
European Patent Office, European Search Report for European Application No. 11191184.8, titled "Bladeless Obturator", dated Feb. 23, 2012.
European Patent Office, European Search Report for European Application No. 11191189.7, titled "Bladeless Obturator", dated Feb. 24, 2012.
European Patent Office, European Search Report for European Application No. 11191175.6, titled "Bladeless Obturator", dated Feb. 21, 2012.
International Searching Authority, International Search Report and Written Opinion for International Application No. PCT/US2012/036119, title "Low-Profile Surgical Universal Access Port", dated Nov. 7, 2012.
European Patent Office, Invitation to Pay Additional Fees for International Application No. PCT/US2012/036119, titled "Low-Profile Surgical Universal Access Port", dated Jul. 13, 2012.
European Patent Office, European Search Report for European Application No. 12187933, titled "Insufflating Optical Surgical Instrument", dated Nov. 20, 2012.
European Patent Office, European Search Report for European Application No. 12187929, titled "Insufflating Optical Surgical Instrument", dated Nov. 20, 2012.
European Patent Office, European Search Report for European Application No. 12186716.2, titled "Bladeless Optical Obturator", dated Mar. 7, 2013.
European Patent Office, European Search Report for European Application No. 12186717.0, titled "Bladeless Optical Obturator", dated Mar. 7, 2013.

(56) References Cited

OTHER PUBLICATIONS

European Patent Office, European Search Report for European Application No. 12186712.1, titled "Bladeless Optical Obturator", dated Mar. 7, 2013.
European Patent Office, European Search Report for European Application No. 12186720.4, titled "Bladeless Optical Obturator", dated Mar. 7, 2013.
International Searching Authority, International Search Report and Written Opinion for International Application No. PCT/US2013/023458 titled "Adaptable Obturator for Various Sized Trocars", dated Mar. 19, 2013.
European Patent Office, European Search Report for European Application No. 12186722.0, titled "Bladeless Optical Obturator", dated Mar. 20, 2013.
European Patent Office, European Search Report for European Application No. 12186721.2, titled "Bladeless Optical Obturator", dated Mar. 22, 2013.
European Patent Office, European Search Report for European Application No. 12186723.8, titled "Bladeless Optical Obturator", dated Mar. 22, 2013.
European Patent Office, European Communication pursuant to Article 94(3) EPC for European Patent Application No. 12186717 .0, titled "Bladeless Optical Obturator", dated Mar. 26, 2013.
Yang, Guoqing, Hong Jun, Zhu, Linbo, Li Baotong, Xiong Meihua, and Wang Fei, Chinese Journal of Mechanical Engineering, (vol. 26, No. 3,2013), Three-Dimensional Finite Element Analysis of the Mechanical Properties of Helical Threat Connection, Revised Jan. 28, 2013, Accepted Feb. 27, 2013.
Taut, Inc., ADAPT—Asymmetrical Dilating Access Port, Geneva Illinois.
Karl Storz, The Karl Storz Ternamian EndoTIP (TM) System, date: Aug. 27, 2001.
Karl Storz, Zerocart Trocar with eccentric tip, Recklinghausen, Germany, date Mar. 7, 2001.
Ethicon Endo-Surgery, Inc., Endopath Minimally Invasive Access, date: 2001.
European Patent Office, European Search Report for European Patent No. 15184957, dated Dec. 1, 2015.
U.S. Appl. No. 10/489,403, filed Mar. 11, 2004; Title: Bladeless Obturator.
U.S. Appl. No. 10/514,313, filed Nov. 12, 2004; Title: Blunt Tip Obturator.
U.S. Appl. No. 10/956,167, filed Oct. 3, 2003; Title: Bladeless Optical Obturator.
U.S. Appl. No. 10/745,262, filed Dec. 23, 2003; Title: Catheter With Conduit Traversing Tip.
U.S. Appl. No. 11/868,883, filed Oct. 8, 2007; Title: Visual Insufflation Port.
U.S. Appl. No. 10/346,846, filed Jan. 17, 2003; Title: Surgical Access Apparatus and Method.
U.S. Appl. No. 10/805,864, filed Mar. 22, 2004; Title: Surgical Access Port and Method.
The International Bureau of WIPO, International Preliminary Report on Patentability for international application No. PCT/US2005/022716, dated Jan. 18, 2007.
International Bureau of WIPO, The International Preliminary Report on Patentability for International Application No. PCT/US2005/0022716 titled "Insufflating Optical Surgical Instrument", dated Jan. 18, 2007, 11 pgs.
European Patent Office, European Search Report for European Patent No. 15184957, titled "Insufflating Optical Surgical Instrument," dated Dec. 1, 2015, 5 pgs.
European Patent Office, European Search Report for European Patent No. 15185511.1, titled "Visual Insufflation Port," dated Jan. 14, 2016, 4 pgs.
European Patent Office, European Search Report for European Patent No. 18155145.8, titled "First Entry Trocar System," dated Apr. 9, 2018, 6 pgs.

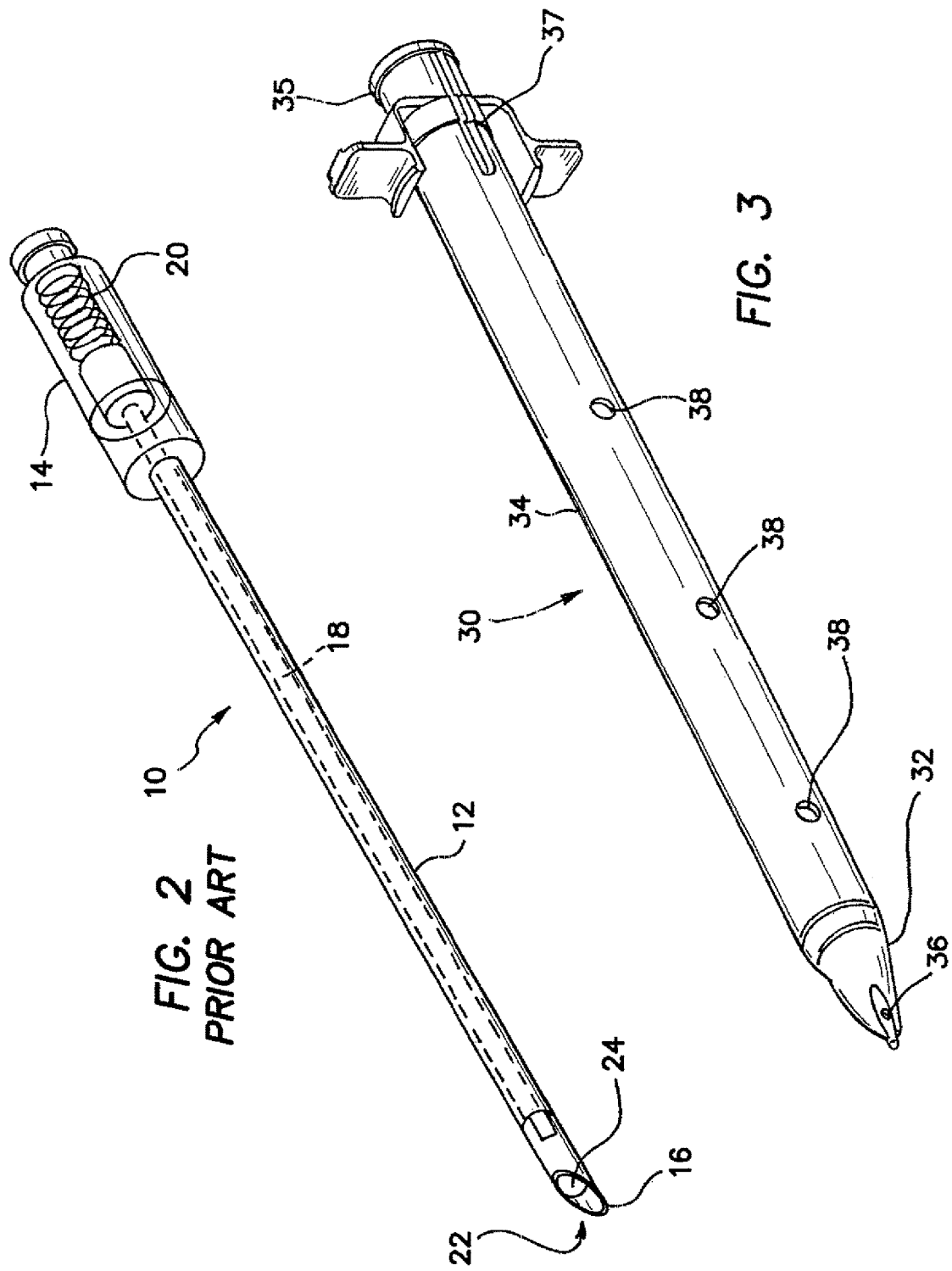

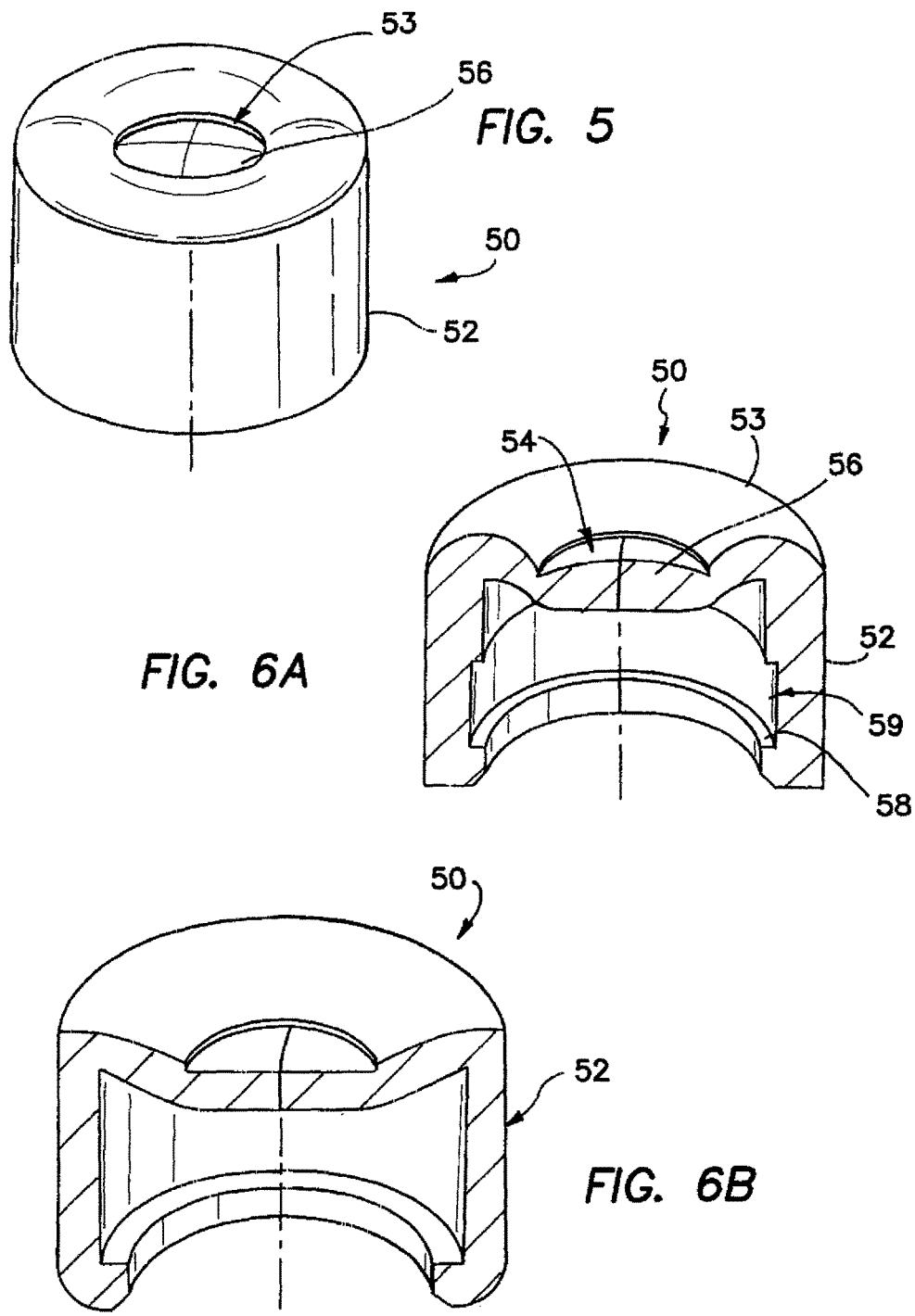

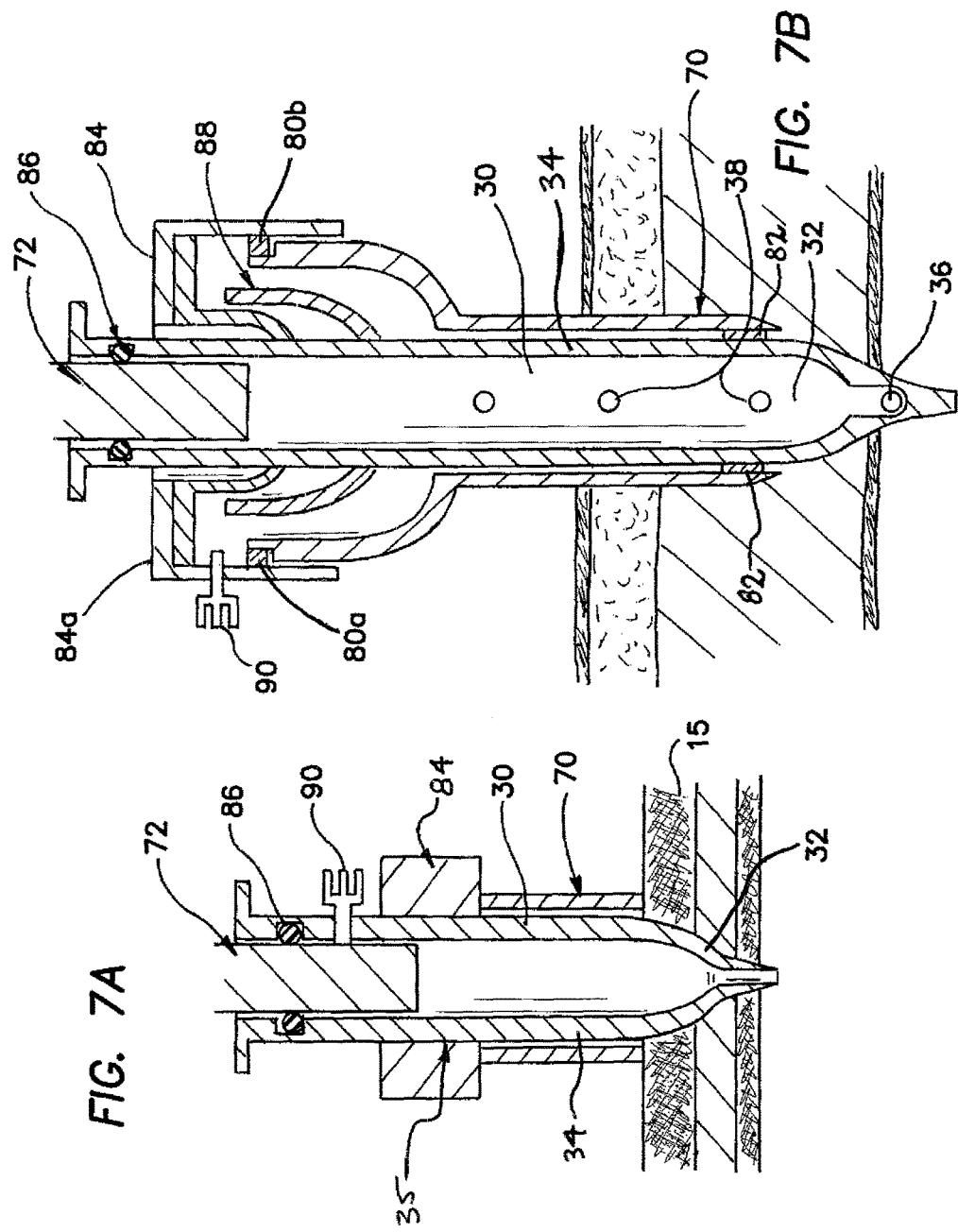

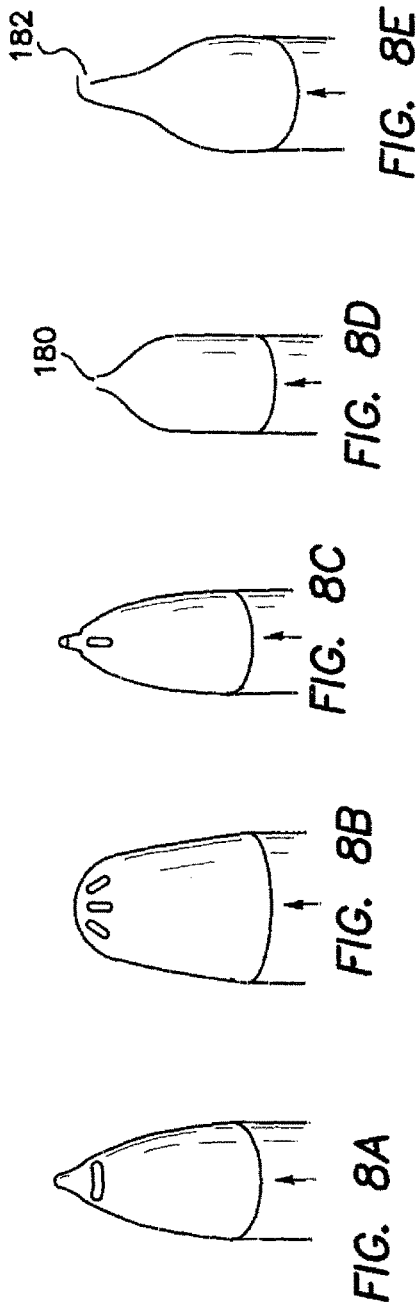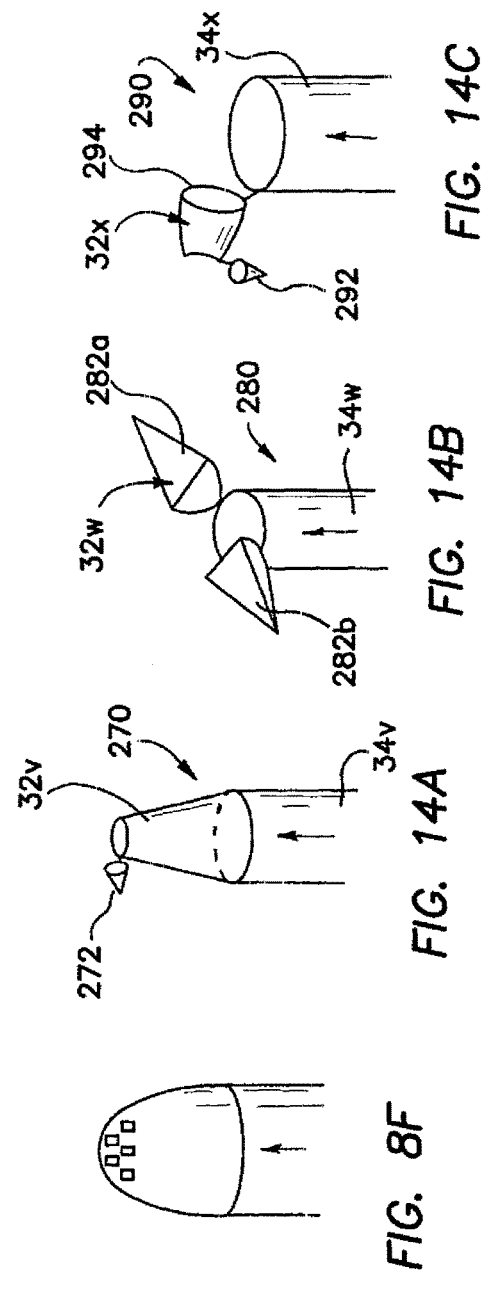

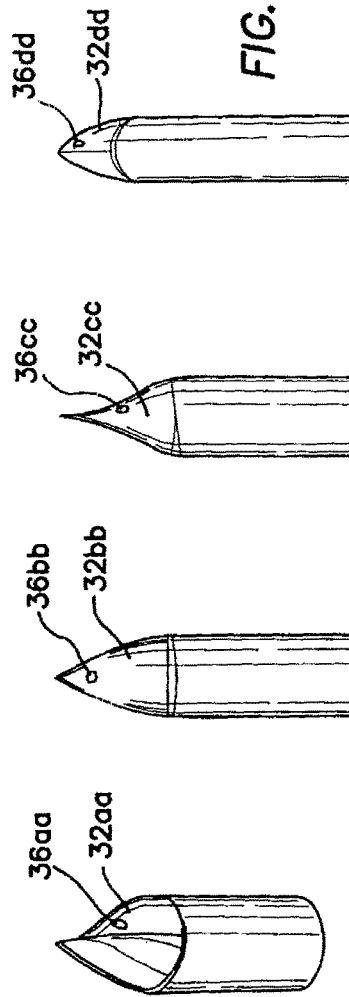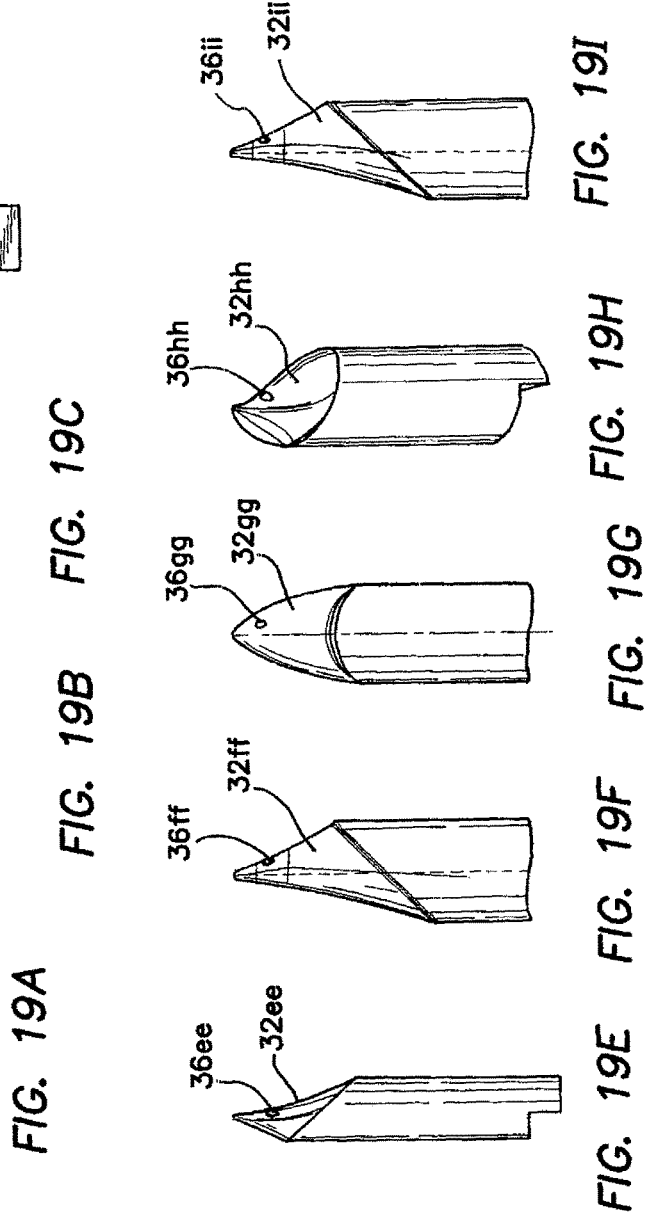

INSUFFLATING OPTICAL SURGICAL INSTRUMENT

CROSS-REFERENCE TO RELATED APPLICATIONS

This application is a continuation of co-pending U.S. patent application Ser. No. 13/356,260 filed on Jan. 23, 2012 now U.S. Pat. No. 9,155,558 issued Oct. 13, 2015 entitled "Insufflating Optical Surgical Instrument" which is a continuation of U.S. patent application Ser. No. 12/766,118, filed Apr. 23, 2010, now U.S. Pat. No. 8,128,590 issued Mar. 6, 2012 entitled "Insufflating Optical Surgical Instrument", which is a continuation of U.S. patent application Ser. No. 11/170,567, filed Jun. 29, 2005, now U.S. Pat. No. 7,708,713, issued May 5, 2010, entitled "Insufflating Optical Surgical Instrument", which is a non-provisional application claiming the priority and benefit of provisional application Ser. No. 60/584,302, filed on Jun. 29, 2004, entitled "Insufflating Optical Surgical Instrument" and is also a continuation-in-part of U.S. patent application Ser. No. 10/956,167, filed on Oct. 1, 2004, entitled "Bladeless Optical Obturator" now U.S. Pat. No. 7,947,058 issued on May 24, 2011 which claims benefit and priority to provisional application Ser. No. 60/508,390 filed on Oct. 3, 2003 all of which are fully incorporated herein by reference in their entireties.

FIELD OF THE INVENTION

This invention generally relates to surgical instruments and, in particular, to surgical instruments providing visual entry and visual insufflation.

BACKGROUND OF THE INVENTION

Laparoscopic surgery of the abdominal area typically requires the introduction of an insufflation gas into the peritoneal cavity of the patient. The insufflation gas is usually pressurized to about 10 mm Hg above atmospheric pressure. This in turn lifts the abdominal wall away from the organs underlying it. Cannulas having seals are then placed at various locations through the abdominal wall to allow the use of a laparoscope and operating instruments. It is well known that establishing access to a non-inflated peritoneal cavity can be a very dangerous part of any laparoscopic procedure. The most common method to achieve insufflation is to pass a sharp needle through the abdominal wall and into the abdominal region, and then inject a gas through the needle and into the region thereby creating an enlarged or ballooned cavity to accommodate a laparoscopic procedure. Unfortunately, insertion of the needle has been required without any visual aid to facilitate location of the sharp needlepoint. In order to reduce the probability of inadvertent penetration of delicate internal organs in this "blind" procedure, the sharp insufflation needle has been provided with a spring-loaded and retractable safety mechanism.

The safety mechanisms associated with most insufflation needles consist of a blunt or rounded member disposed within the lumen of the needle, and biased by a spring to an extended position beyond the needle tip. This spring must be responsive to the insertion pressure during placement of the needle but must be capable of immediately moving forward when that pressure is relieved. This is a highly mechanical event at best and offers less than optimal arrangement. As pointed out above, a drawback of this procedure is it is performed blindly. A consequence of this blind insertion is the surgeon may inadvertently damage the organs and tissues underlying the abdominal wall such as major blood vessels and the intestinal tract. Once access is gained, it can take several minutes for the gas to insufflate the abdomen and while this is happening the surgeon may be unaware of any complications caused by the insertion of the needle.

Another commonly used method of gaining initial access to the peritoneal cavity is by using a procedure known as the Hasson technique. This method involves making a mini-laparotomy and using the fingers to bluntly dissect the tissues of the abdominal wall and thereby creating an access similar to an open surgical procedure. This method is generally considered to be safer but not without risks, and results in an access site that is not well suited for the subsequent introduction and use of a laparoscopic cannula. The cannula is typically held in place with an additional device that allows the cannula to be tied down with sutures to prevent it from slipping out of the abdominal wall. This also leaves a large defect and is difficult to perform in large abdominal walls.

Some surgeons have used trocars designed for use with laparoscopes for the initial entry into the peritoneal cavity. These devices allow the placement of a laparoscope through the internal diameter of the trocar and have a trocar tip that is made of clear plastic to allow the surgeon to visualize the passage of the tip through the abdominal wall. However, in order to allow the subsequent introduction of insufflation gas through the cannula, the trocar and cannula must be inserted all the way through the wall of the abdomen and this in turn can be potentially dangerous as the tip of the trocar may have to advance as much as one inch beyond the distal surface of the abdominal wall and into the underlying anatomical structures. As such, there remains a need in the art for an improved surgical instrument that provides visual entry and visual insufflation, and that minimizes the risks of damaging organs, tissues and vessels underlying a body wall.

SUMMARY OF THE INVENTION

The invention is directed to surgical instruments providing visual entry and visual insufflation with minimal risks of injury to organs, tissues and vessels underlying a body wall. It is appreciated that the concept of the invention may be applied to any surgical instrument that provides the ability to insufflate under direct vision of the site of insufflation, regardless of the size of the instrument and the type of insufflation fluid. More specifically, the surgical instrument provides the ability to transfer an insufflation fluid such as $CO_2$ or saline from outside a patient to inside a surgical cavity under vision. The insufflation fluid may be transferred inside a lumen, along a body channel or through a coiled tube of a surgical instrument or scope used for vision.

In a first embodiment of the invention, an insufflating surgical instrument adapted for movement across an abdominal wall to insufflate an abdominal region of a patient is disclosed comprising a shaft having an insufflation channel extending along an axis between a proximal end and a distal end, the insufflation channel being adapted for connection to a source of fluid under pressure at the proximal end. The insufflating surgical instrument further comprises a tip at the distal end of the shaft and at least one vent hole formed at the tip or the shaft being in connection with the insufflation channel and being adapted to expel the fluid under pressure to insufflate the abdominal region. In one aspect, at least one of the tip and the shaft is formed of a transparent material to facilitate visualization of the abdominal wall and the abdominal region. With this aspect, the shaft and the tip are configured to enable insertion of a laparoscope. In particular, the shaft includes a lumen extending along the axis between the proximal end and the distal end to enable insertion of the laparoscope. The lumen and insufflation channel may be formed as separate channels or as one shared channel. The insufflating surgical instrument may further comprise a second vent hole being in connection with the insufflation channel and formed along the shaft. It is appreciated that the tip may be blunt, the shaft and the tip may be integrally formed, and the vent hole may be of any geometric shape including round, oval, square and rectangular. With this aspect, at least one of the tip and the shaft may be formed of a translucent or a transparent material such as polycarbonate. The blunt tip may further comprise a marker to indicate when the vent hole has been positioned for insufflation. More specifically, the marker indicates the point where the vent hole has penetrated the abdominal wall. The shaft of the invention may further comprise a scope lock to prevent the laparoscope from being inserted too far into the shaft and block at least one of the insufflation channel and the vent hole. In another aspect, the tip may be sharp, pointed or bladed to facilitate penetration of body tissue.

The insufflating surgical instrument may further comprise a seal housing disposed at the proximal end of the shaft. The seal housing comprises a septum seal and a plurality of leaflets forming an instrument seal in the presence of a laparoscope, and providing a zero seal in the absence of an instrument. The thickness of the leaflets may be formed to a desired dimension to create a pressure release mechanism that inverts and releases pressure if the abdominal pressure within the patient undergoes a sudden spike. The septum seal may be formed of an elastomeric material including Kraton, silicone and the like. The seal housing may further comprise a duckbill or a double duckbill valve distal of the leaflets to further limit gas or fluid escape.

In another aspect of the invention, an insufflating surgical instrument adapted for penetrating an abdominal wall to insufflate an abdominal region of a patient is disclosed comprising a shaft having an insufflation channel extending along an axis between a proximal end and a distal end, the insufflation channel being adapted for connection to a source of fluid under pressure at the proximal end. The insufflating surgical instrument further comprises a tip at the distal end of the shaft, the tip having a first, closed position during penetration of the abdominal wall and a second, opened position to expel the fluid under pressure to insufflate the abdominal region after penetration of the abdominal wall. The tip may be a flip-top that automatically opens upon traversing the abdominal wall or a flapper valve that opens to the second position when gas or fluid is introduced at the source and into the insufflation channel. The insufflating surgical instrument may further comprise a retention member for connecting the shaft and the flip-top. The flip-top may be a two-piece flip-top, the flapper valve may be a reverse flapper valve or a spring-based flapper valve, and the retention member may be one of a spring, a spring wire, an offset hinge or a living hinge. In another aspect, the tip may comprise at least two petals that reposition to the side of the shaft in the second insufflation position.

Another aspect of the invention is a laparoscopic insufflating surgical instrument adapted for movement across an abdominal wall to insufflate an abdominal region of a patient comprising an elongate tube having a distal tip, an insufflation channel extending between a proximal end and a distal end, the elongate tube being adapted for connection to a source of fluid under pressure at the proximal end, and being adapted at the distal end to expel the fluid under pressure to insufflate the abdominal region, and an optical element disposed at the distal end of the elongate tube to facilitate visualization of the abdominal wall and the abdominal region. With this aspect, the distal tip is defined by a curved surface, the distal tip being translucent or transparent, and the optical element being a light or an endoscope. It is appreciated that the insufflating surgical instrument may be an insufflating Veress needle.

Another aspect of the invention is directed to a laparoscopic insufflating surgical instrument adapted for movement across an abdominal wall to insufflate an abdominal region of a patient comprising an elongate tube having a proximal end and a distal end, an optical element disposed at the distal end of the elongate tube to facilitate visualization of the abdominal wall and the abdominal region of the patient, and an insufflation channel having a proximal end and a distal end extending along the proximal end and the distal end of the elongate tube, the insufflation channel being adapted for connection to a source of fluid under pressure at the proximal end, and to expel the fluid under pressure to insufflate the abdominal region at the distal end. With this aspect, the insufflation channel is formed into a coil around the elongate tube. It is further appreciated that the distal end of the elongate tube may be tapered to form a generally cone-tipped end.

In yet another aspect of the invention, there is disclosed an insufflating surgical instrument adapted for movement across an abdominal wall to insufflate an abdominal region of a patient, the surgical instrument comprising an insufflating cannula having a wall forming a first lumen extending along an axis between a proximal end and a distal end, and a first insufflation channel formed in the wall extending along the axis between the proximal end and the distal end and being adapted for connection to a source of fluid under pressure at the proximal end. The insufflating surgical instrument further comprises an insufflating trocar having a shaft with a second lumen extending along the axis between a proximal end and a distal end, a second insufflation channel formed at the distal end and being adapted for alignment with the first insufflation channel of the cannula to expel the fluid under pressure to insufflate the abdominal region, and a tip at the distal end of the shaft, and at least one vent hole formed at the tip of the trocar being in connection with the second insufflation channel of the trocar. The insufflating surgical instrument may further comprise a laparoscope adapted for insertion at the proximal end of the trocar and advanced to the distal end as the trocar is placed through the abdominal wall.

Another aspect of the invention is directed to a method for using an insufflating surgical instrument to create access across an abdominal cavity and to insufflate an abdominal region of a patient, the method comprising providing a transparent shaft having a lumen and an insufflation channel extending along an axis between a proximal end and a distal end, the insufflation channel being adapted for connection to a source of fluid under pressure at the proximal end, a tip at the distal end of the shaft, and at least one vent hole formed at the tip or the shaft being in connection with the insufflation channel and adapted to expel the fluid under pressure to insufflate the abdominal region; moving the shaft across the abdominal wall to place the distal end of the shaft in the abdominal region; and expelling gas or fluid under pressure through the insufflation channel to insufflate the abdominal region of the patient. The method for using the insufflating surgical instrument may further comprise the step of visualizing the abdominal cavity through the lumen of the shaft.

These and other features of the invention will become more apparent with a discussion of the various embodiments in reference to the associated drawings.

BRIEF DESCRIPTION OF THE DRAWINGS

The accompanying drawings, which are included in and constitute a part of this specification, illustrate the embodiments of the invention and, together with the description, explain the features and principles of the invention. In the drawings:

FIG. 2 illustrates a perspective view of an insufflation needle of the prior art.

FIG. 3 illustrates a perspective view of an insufflating optical trocar in accordance with a first embodiment of the invention.

FIG. 5 illustrates a perspective view of a septum seal for use with the insufflating optical trocar of the invention.

FIG. 6(a)-6(d) illustrate cross-sectional views of the septum seal for use with the insufflating optical trocar of the invention.

FIGS. 7(a) and 7(b) illustrate the insufflating optical trocar and cannula of the invention.

FIGS. 8(a)-8(f) illustrate different geometric shapes and patterns of the vent hole of the invention.

FIGS. 14(a)-14(c) illustrate flip-top or flip-tip designs of insufflating optical surgical instruments in accordance to additional embodiments of the invention.

FIGS. 19(a)-19(i) illustrate additional tip designs in accordance to other aspects of the invention to facilitate penetration of body tissue.

DETAILED DESCRIPTION OF THE INVENTION

Figure 1:
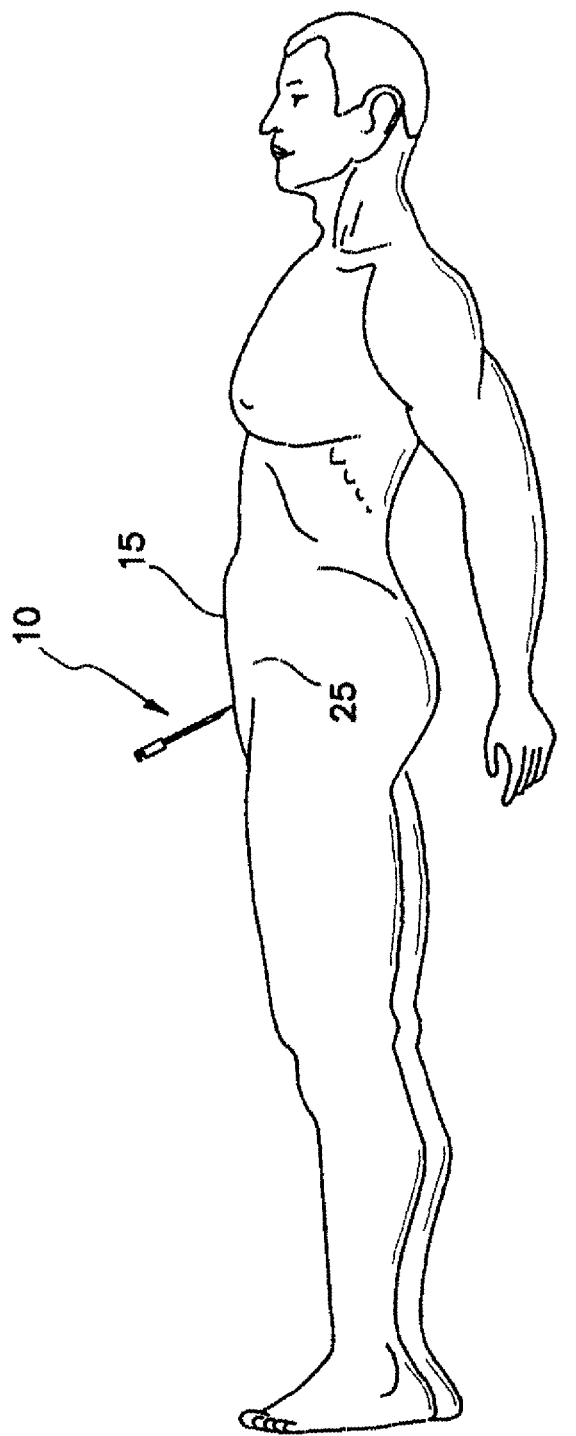
FIG. 1 illustrates a typical laparoscopic abdominal surgery of the prior art.

Referring to FIG. 1, there is shown a typical laparoscopic abdominal surgery where an inflation needle 10 is inserted through a body or abdominal wall 15 and into an abdominal cavity 25. A gas is passed through the needle 10 to create a space within the abdominal cavity 25. This procedure is referred to as insufflation. The needle 10 is referred to as an insufflation needle and the gas supply is referred to as an insufflation gas. The insufflation needle 10 is placed through the body wall 15 blindly. In other words, there is no direct visualization of the procedure from the inside of the body wall 15. As explained earlier, the current procedure may inadvertently damage organs and tissues underlying the body or abdominal wall 15 such as major blood vessels and the intestinal tract. It is not uncommon for there to be internal structures attached to the internal side of the body wall 15. This is especially so in the case of the abdominal cavity 25. Portions of the intestines, colon and bowel may be attached to the abdominal wall 15. These attachments are referred to as adhesions.

Adhesions represent a potential complication in laparoscopic surgery. This is especially the case as the procedure is initiated using a sharp or pointed instrument such as the insufflation needle 10. The delicate internal structures that may be attached by adhesions may inadvertently be pierced by the introduction of the insufflation needle 10. This can be very serious and may go undetected for some time.

Referring to FIG. 2, the typical insufflation needle 10 comprises an elongate tubular body 12, a proximal connecting housing 14, a sharp, pointed distal tip 16 and a spring, biased internal blunt core 18 with a blunt end 24 that extends beyond the sharp distal tip 16 under the influence of an extended compression spring 20. A typical placement of the insufflation needle 10 requires a user to push the sharp distal tip 16 into the abdominal wall 15, which pushes the blunt core 18 proximally, then continues to push until the distal end 22 is through the body wall 15. At that point, the blunt end 24 moves forward and thereby protects delicate structures from being inadvertently punctured by the sharp distal tip 16 of the needle 10. The safety of such a device depends to a large extent on the design and integrity of the spring 20 since the sharp distal tip 16 remains within the established internal region or body cavity 25.

Referring to FIG. 3, there is shown a perspective view of an insufflating optical instrument or trocar 30 in accordance with a first embodiment of the invention. The insufflating optical trocar 30 is designed to separate tissue fibers during insertion through the body wall 15. The insufflating optical trocar 30 includes a shaft 34 having a lumen extending substantially along an axis between a proximal end and a distal end, a handle 35 disposed at the proximal end of the shaft 34, and a blunt tip 32 disposed at the distal end of the shaft 34. The shaft 34 of the insufflating optical trocar 30 is sized and configured for disposition within a working channel of a cannula system as described in co-pending application Bladeless Optical Obturator, which is herein incorporated by reference. With this disposition, the insufflating optical trocar 30 functions to penetrate a body or abdominal wall to provide the cannula with access across the body wall 15 and into the body cavity 25, such as the peritoneal or abdominal cavity.

In one aspect of the invention, the shaft 34 and tip 32 are integrally formed of a transparent material to enable visualization of tissue during the insertion of the insufflating optical trocar 30 through the body wall 15. The insufflating optical trocar 30 is configured to enable the insertion of a conventional laparoscope, which typically includes an imaging element and fiber optic light fibers. The tip 32 further includes at least one vent hole 36, and preferably two or more vent holes one on each side of the tip 32, for the insufflation gas to transfer from the inside of the trocar 30 into the body or abdominal cavity 25. The vent hole 36 may be chamfered on the proximal side such that the vent hole does not core tissue as the insufflating optical trocar 30 enters through the body wall 15.

The shaft 34 includes at least one shaft vent 38 and preferably a plurality of shaft vents 38 along the axis between the proximal end and the distal end. It is appreciated that vent holes 36 and shaft vents 38 may be of any geometric shape including round, oval, square, rectangular, etc., as illustrated in FIGS. 8(a)-8(c) and may be configured in different patterns such as a waffle pattern as illustrated in FIG. 8(f). Furthermore, the tip 32 may be an open tip 180 or a non-coring tip 182 as illustrated in FIGS. 8(d) and 8(e), respectively, to allow the transfer of insufflation gas into the body cavity 25. Advantages of the shaft vents 38 include supporting a plurality of core pins during the injection molding process of the shaft 34 to provide a uniform part thickness, and allowing the insufflation gas to transfer from the inner diameter of the cannula and seal housing into the inner diameter of the insufflating optical trocar 30 and consequently out of the vent holes 36 at tip 32.

Figure 4A:
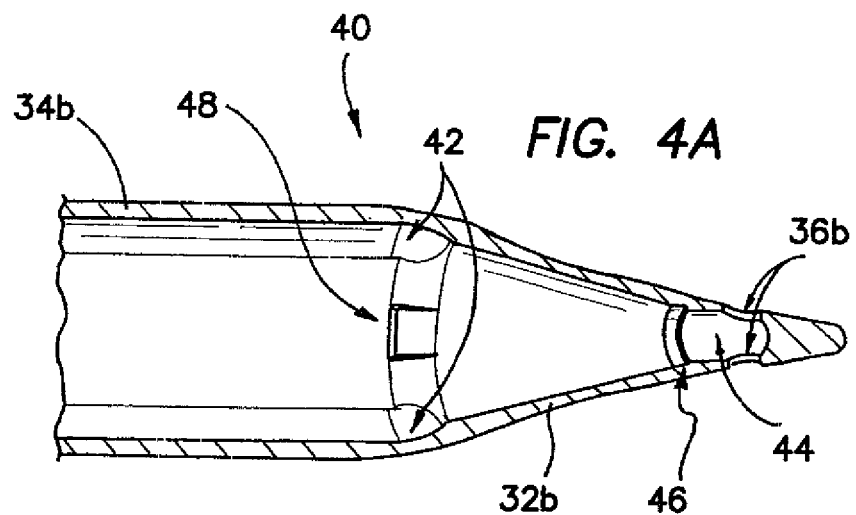
FIGS. 4(a) and 4(b) illustrate cross-sectional views of an insufflating optical trocar in accordance with another embodiment of the invention.
Figure 4B:
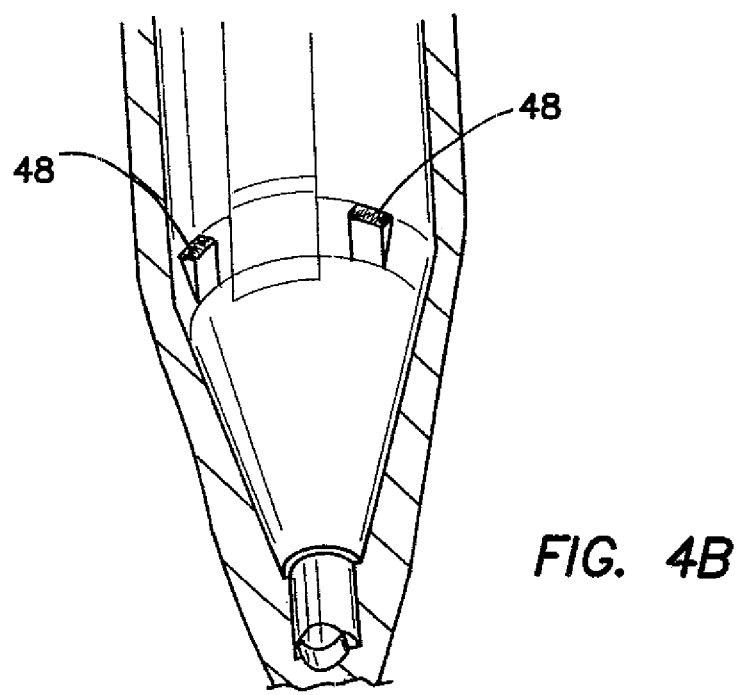
Figure 6C:
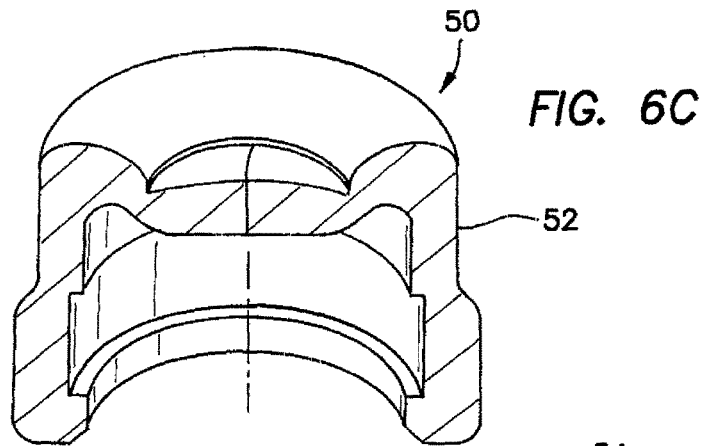
Figure 6D:
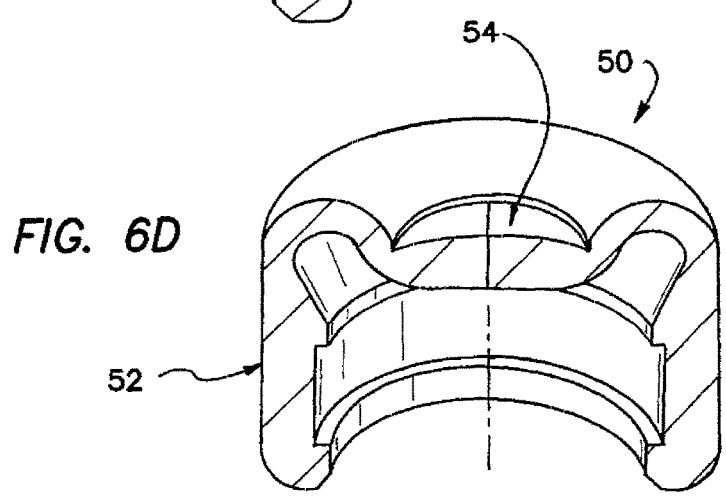

Referring to FIGS. 4(a) and 4(b), there are shown side cross-sectional views of an insufflating optical trocar 40 in accordance with another embodiment of the invention. The insufflating optical trocar 40 includes a shaft 34b having a lumen extending substantially along an axis between a proximal end and a distal end, and a blunt tip 32b disposed at the distal end. The insufflating optical trocar 40 further includes at least one gas channel 42 extending along the length of the shaft 34b to provide rapid gas transfer through the insufflating optical trocar 40 when a scope has been placed within the inner diameter. It is appreciated that there may be more than one gas channel 42 extending along the length of the shaft 34b to provide rapid gas transfer through the trocar 40. It is further appreciated that the gas channel 42 may be formed as a separate channel or as the same channel for inserting the scope, that is, by increasing the inner diameter of the shaft 34b to be bigger than the diameter of the scope. More specifically, even if the scope and gas share the same channel, the gas channel 42 assures that there is sufficient cross-sectional area for the gas to travel along the side of the scope and down to the vent hole(s) 36b even when the scope is in place.

The tip 32b may further include a marker 46 to be used as a visible reference point. The marker 46, together with an area indicated by reference number 44 as shown in FIG. 4A, depict the down vent of the insufflating optical trocar 40 that transfers the gas from the gas channel 42 of the trocar 40 to the vent holes 36b at tip 32b. For example, as the trocar 40 is being placed through the abdominal wall 15, at some point the tip 32b of the trocar 40 will penetrate the peritoneum. Once the peritoneum can be seen through the tip 32b and once the peritoneum is above the visible marker 46, the insufflation gas can be turned on and insufflation can begin. As such, this marks the point where the vent hole 36b is within the abdominal cavity. Once the insufflation gas has created sufficient space between the abdominal wall and the organ bed, the remainder of the insufflating optical trocar 40 including the cannula system can then be fully inserted to an operative position.

The insufflating optical trocar 40 may further include a scope stop 48 as illustrated in FIG. 4(b) to keep a scope from being inserted into the taper of the inner diameter of the trocar 40. The scope stop 48 may further include a ledge that further prevent the possibility of the scope from being inserted too far into the trocar and consequently block the distal portion of the gas channel 42.

Referring to FIG. 5, there is shown a perspective view of a septum seal 50 to be used with the insufflating optical trocar of the invention. The septum seal 50 includes a tubular body 52, a septum ring 53 and a plurality of leaflets 54 formed by a slit 56 providing an instrument seal when a scope is inserted into the insufflating optical trocar and a zero seal when the scope is withdrawn from the trocar. In addition, the thickness of the leaflets 54 can be controlled such that a pressure release mechanism can be created and consequently allowing the leaflets 54 to invert and release pressure if the abdominal pressure within the patient undergoes a sudden spike. Referring to FIGS. 6(a)-6(d), there are shown cross-sectional views of the septum seal 50 of FIG. 5. The septum seal 50 further includes a retaining ledge 58, which allows the septum seal 50 to be attached to the cap or handle 35 of the insufflating optical trocar, and also serves as a sealing surface. Reference number 59 illustrates a sealing surface between the septum seal 50 and the cap or handle of the insufflating optical trocar. The septum seal 50 may further comprise a duckbill or double duckbill valve placed distally of the leaflets 54 to further limit gas or fluid escape.

During use, the insufflating optical trocar 30 is first inserted into a seal housing 84 and cannula 70 as illustrated in FIG. 7(a). A conventional laparoscope 72 is then inserted into the proximal end of the insufflating optical trocar 30 and advanced to the distal end of the trocar 30. An endoscopic video camera is attached to the proximal end of the laparoscope 72. The trocar 30 is then axially advanced by the surgeon through the body wall 15. As the surgeon advances the cannula 70 and trocar 30 through the body wall 15, the surgeon can visually observe tissue of the body wall 15 as it is being separated via a video monitor, which is connected to the endoscopic video camera. The surgeon can also readily determine when the body wall 15 has been completely traversed by the trocar 30. Once the trocar 30 has traversed the body wall 15, the trocar 30 and laparoscope 72 may be removed which leaves the cannula 70 disposed across the body wall 15 to provide an access channel into the body cavity 25 for the insertion of laparoscopic instrumentation.

As illustrated in FIG. 7(a), the insufflating optical trocar 30 is designed for use with the seal housing 84 and cannula 70. The tip 32 may be blunt and does not include any sharp edges, piercing points or blades. With this aspect of the invention, the tip 32 of the bladeless insufflating optical trocar 30 is transparent and generally hollow. This enables a clear view through the distal tip of the insufflating optical trocar 30 and increases the visibility of tissue as it is being traversed. The obturator shaft 34 with the integral tip 32 may be formed of a transparent material such as polycarbonate. The septum seal 50, which may be formed of a material such as Kraton, silicone and the like, may be snap fitted onto the proximal end of the obturator shaft 34. The seal housing 84 may further include a handle attachment 35 including a cannula seal, which may be formed of a plastic material such as polycarbonate, that operates to attach the trocar 30 to the cannula 70 so as to maintain axial position during insertion.

The diameter of the shaft 34 can range from about 2 mm to 50 mm and is designed to fit within the seal housing 84 and cannula 70.

Referring to FIG. 7(b), the cannula 70 is designed to releasably attach to the seal housing 84 via cannula seal 80a, 80b. As the shaft 34 is inserted into the seal housing 84 and cannula 70, the cannula seal 80a, 80b passively engages the seal housing 84 and serves to axially lock the shaft 34 to the seal housing 84 and cannula 70. To release the shaft 34 from the seal housing 84 and cannula 70, outboard tabs on shaft 34 are depressed inwardly and the shaft 34 is then free to be slidably removed. The shaft 34 includes axial key members 37 (see FIG. 3) at its proximal end which are designed to mate with axial keyways on the seal housing 84. As the shaft 34 is inserted into the seal housing 84 and cannula 70, the shaft 34 is rotated slightly to align key members 37 with the keyways and then advanced until the cannula seal 80a, 80b engages the seal housing 84. The key members 37 serve to rotationally index the shaft 34 to the seal housing 84. In another aspect, cannula 70 may further include distal cannula seal 82 formed at a distal portion of cannula 70 and shaft 34 so as to further limit gas or fluid escape.

In another aspect of the invention, the insufflating optical trocar 30 may include a laparoscope lock 86 having an elastomeric element. The addition of the elastomeric element would enhance the frictional engagement with the laparoscope 72. An example of an elastomeric element would be a silicone O-ring sized with an inside diameter smaller than the outside diameter of the laparoscope 72. The laparoscope lock 86 could either rotate freely to enable the laparoscope 72 to rotate freely relative to the shaft 34 or the laparoscope lock 86 could be rotationally fixed to prevent the laparoscope 72 from rotating relative to the shaft 34.

In another aspect of the invention, a process of placing and using the insufflating optical trocar of the invention is described. First, the skin around the area to be operated on is incised appropriately for the size of the cannula 70. An insufflation gas line 90, which is attached to the seal housing 84, the insufflating optical trocar 30 and the laparoscope 72 are then inserted into the cannula 70. At this point the gas supply is still turned off. The assembled device is then advanced through the body or abdominal wall 15 under direct vision until it is observed that just the tip 32 of the device has penetrated the peritoneal cavity. The device is then held in place and the flow of insufflation gas is begun. The gas will flow through the tip 32 and into the peritoneal cavity until the cavity is sufficiently distended by gas pressure. The surgeon then completes the insertion of the insufflating optical trocar 30 until the cannula 70 is in an appropriate or desired position. The insufflating optical trocar 30 and laparoscope 72 may then be removed. At this point, the surgeon may elect to reinsert just the laparoscope 72 through the seal housing 84 and thereby allow observation of the abdominal cavity and subsequent insertions of additional laparoscopic instrumentation.

As explained earlier, an indicator line or marker 46 as shown in FIG. 4(a) may be located on tip 32 to be viewed by laparoscope 72 to indicate when the device has advanced far enough into the body cavity to begin insufflation. The coincidence of anatomical features with the indicator line or marker 46 may indicate the correct position to begin insufflation. The indicator line or marker 46 could be circumferential in nature and when the peritoneal layer, as it is being penetrated, forms a coincident circle with respect to the indicator line 46, the surgeon can begin insufflating. Another method is to employ an O-ring seal 86. Additionally, it is preferred that a zero seal be present on the trocar to prevent escape of the gas when the trocar is used to place cannulas without the laparoscope 72. A double duckbill valve 88 would work well too for this application as would a single duckbill, a flapper valve or a slit valve.

Figure 9:
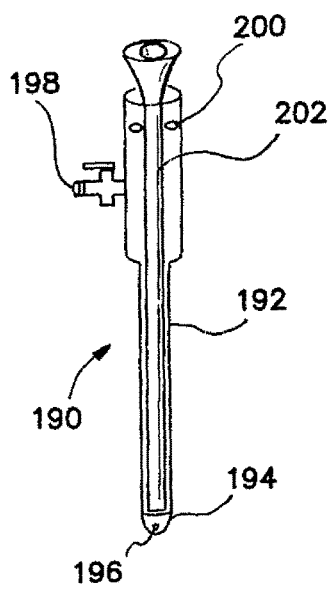
FIG. 9 illustrates an insufflating needle having a transparent distal tip and insufflating vent in accordance with another embodiment of the invention.
Figure 10:
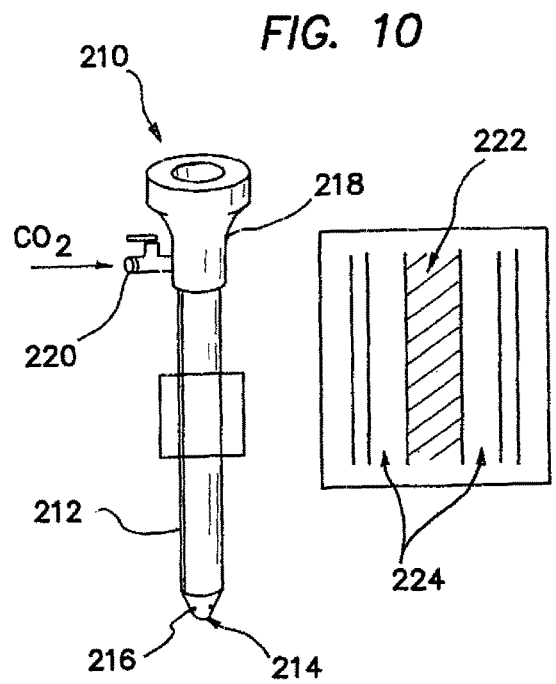
FIG. 10 illustrates an insufflating scope having a transparent distal tip and insufflating vent in accordance with another embodiment of the invention.

It is appreciated that the above-described concept may be applied to any surgical instruments providing visual entry and visual insufflation, regardless of size or type of fluid transfer as further described in the following exemplary embodiments of the invention. For example, FIG. 9 illustrates an insufflating needle 190 in accordance with another aspect of the invention comprising an elongate tubular body 192 having an insufflation channel extending along an axis between a proximal end and a distal end, a transparent distal tip 194 operably attached to the distal end of the tubular body 192, and at least one insufflating vent hole 196 formed at the distal tip 194 or tubular body 192 and being in connection with the insufflation channel. The insufflating needle 190 may further include an insufflation-controlling device 198 such as a stopcock and a sealing mechanism 200 at the proximal end of the tubular body 192. A small diameter scope 202 may be inserted at the proximal end of the tubular body 192 and then advanced to the distal end of the tubular body 192 as the insufflating needle 190 such as an insufflating Veress needle is placed through an abdominal wall. In yet another aspect of the invention as illustrated in FIG. 10, an insufflating scope 210 comprises an elongate body 212 having an insufflation channel 224 extending along an axis between a proximal end and a distal end, a transparent tip 214 operably attached to the distal end of the elongate body 212 and having at least one insufflating vent hole 216 being in connection with the insufflation channel 224, and a handle 218 formed at the proximal end of the elongate body 212. The insufflating scope 210 may further include an insufflation-controlling device 220 such as a stopcock at the proximal end of the elongate body 212 or on the handle 218. The elongate body 212 includes an optical element 222 that directs light to the tip 214 and at least one insufflation channel 224 to transfer the insufflation gas into the surgical cavity.

Figure 11:
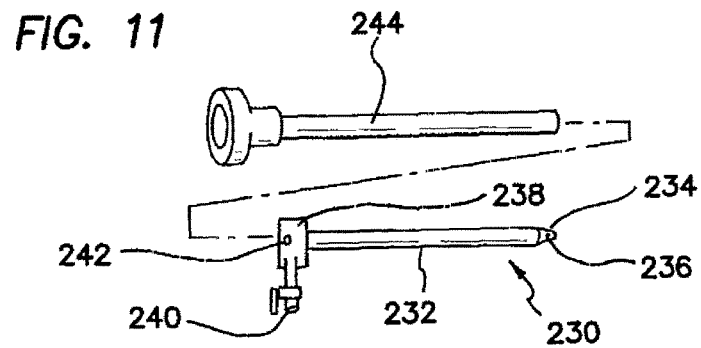
FIG. 11 illustrates an insufflating scope sleeve having a transparent distal tip and insufflating vent in accordance with another embodiment of the invention.

Referring to FIG. 11, there is shown an insufflating scope sleeve 230 in accordance with another embodiment of the invention. The insufflating scope sleeve 230 comprises a flexible sleeve 232 having a proximal end and a distal end, a transparent tip 234 operably attached to the distal end of the flexible sleeve 232 and having at least one insufflating vent hole 236, and a handle 238 attached to the proximal end of the flexible sleeve 232. The insufflating sleeve 230 may further include an insufflation-controlling device 240 such as a stopcock and a sealing mechanism 242 at the proximal end of the insufflating sleeve 230. A scope 244 may be inserted at the proximal end of the insufflating scope sleeve 230 and then advanced to the distal end of the insufflating scope sleeve 230 as the insufflating scope sleeve 230 is placed through an abdominal wall.

Figure 12A:
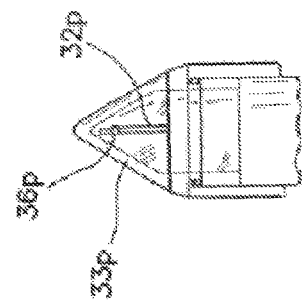
FIGS. 12(a)-12(f) illustrate additional tip designs of an insufflating optical surgical instrument in accordance with additional aspects of the invention.
Figure 12B:
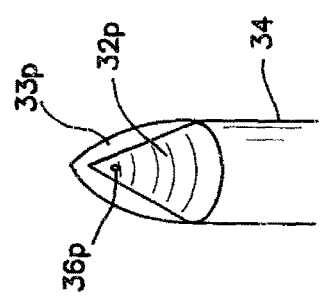
Figure 12C:
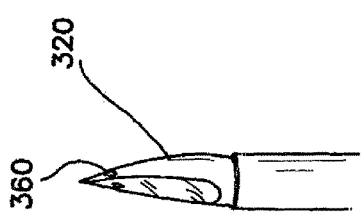
Figure 12D:
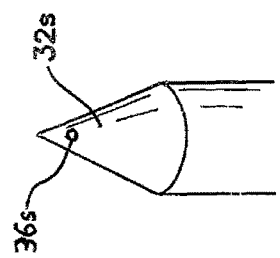
Figure 12E:
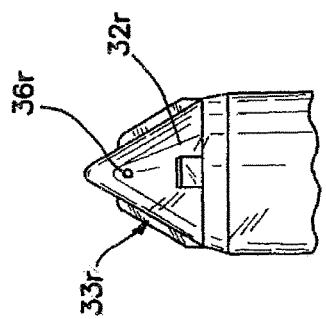
Figure 12F:
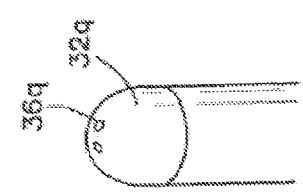

Referring to FIGS. 12(a)-12(f), there are shown additional tip designs 32o-32s in accordance with other aspects of the invention to facilitate penetration of a body tissue. FIG. 12(a) illustrates a spoon-shaped or asymmetric tip 32o having at least one vent hole 36o; FIGS. 12(b) and 12(c) illustrate a generally domed or conical shaped tip 32p having plastic or metal blades 33p along an axis of the shaft and at least one vent hole 36p; FIG. 12(d) illustrates a blunt tip 32q having at least one vent hole 36q; FIG. 12(e) illustrates a generally domed or conical shaped tip 32r having at least one bladed fin 33r and at least one vent hole 36r; and FIG. 12(f) illustrates a generally conical shaped tip 32s having at least one vent hole 36s at the distal tip. It is appreciated that tips 32o, 32p, 32r and 32s have a sharp, pointed or bladed tip and/or edge to facilitate penetration of body tissue. In yet other aspects of the invention, the surface of the tip may have at least one tissue engaging raised pattern on the surface. The surface operates to facilitate insertion of the insufflating surgical instrument or optical trocar with a reduced penetration force and minimize tenting of the body wall. The surface may further facilitate separation of different layers of the body wall and provides proper alignment of the tip between the layers. In another aspect of the invention, the tip may have an outer surface extending distally to a blunt point and includes a pair of side sections separated by an intermediate section, and wherein the side sections extend from the blunt point radially outwardly with progressive positions proximally along the axis. The side sections may include a distal portion in proximity to the blunt point and a proximal portion in proximity to the tubular body, and the distal portion of the side sections being twisted radially with respect to the proximal portion of the side sections.

Figure 13A:
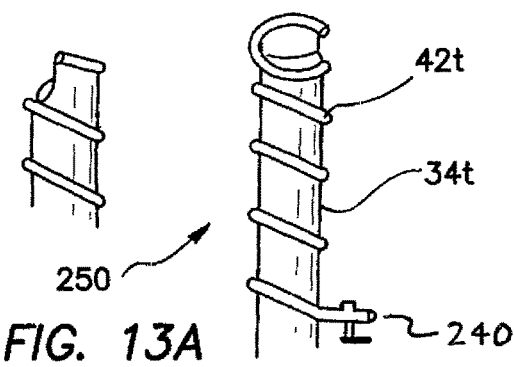
FIGS. 13(a) and 13(b) illustrate a coiled insufflating optical trocar and a coiled insufflating optical trocar with a coiled tip, respectively, in accordance with additional embodiments of the invention.
Figure 13B:
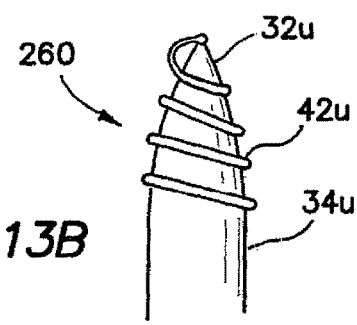

FIGS. 13(a) and 13(b) illustrate a coiled insufflating optical trocar 250 and a coiled insufflating optical trocar with a coiled tip 260, respectively, in accordance with additional embodiments of the invention. The coiled insufflating optical trocar 250 comprises a shaft 34t having a lumen and a hollow coiled tube or gas channel 42t wrapped substantially along the length of the shaft 34t to provide gas transfer into the body cavity. An advantage of this aspect of the invention is coiling also helps to keep the trocar from moving about inside a body cavity. The coiled insufflating optical trocar 250 may further include an insufflation-controlling device 240 such as a stopcock at the proximal end of the coiled insufflating optical trocar 250. A scope may be inserted at the proximal end of the coiled insufflating optical trocar 250 and then advanced to the distal end of the trocar 250 as the trocar 250 is placed through an abdominal wall. The coiled insufflating optical trocar with coiled tip 260 as shown in FIG. 13(b) is similar to the coiled insufflating optical trocar 250 but further includes a tip 32u and a hollow coiled tube or gas channel 42u that wraps around the tip 32u and substantially along the length of the shaft 34u.

Referring to FIGS. 14(a)-14(c), there are shown additional tip designs 32v-32x in accordance to other aspects of the invention. For example, the tip 32v as illustrated in FIG. 14(a) comprises a flip-top 272 and a conical body 270 that operates to move from a first, penetrating position to a second, insufflating position when the body wall has been traversed. The tip 32v may further comprise a retention member for connecting the flip-top 272 and the conical body 270. The retention member may be one of a spring, a spring wire, an offset hinge or a "living" hinge. Other flip-top or flip-tip designs as described in co-pending U.S. patent application Ser. No. 10/805,864, entitled "Surgical Access Port and Method of Using Same," filed Mar. 22, 2004, which is herein incorporated by reference, may also be used with the insufflating concept of the invention. In yet another aspect of the invention, the tip 32w as illustrated in FIG. 14(b) comprises a two-piece flip-top 282a, 282b that operates to move from a first, penetrating position to a second, insufflating position when the body wall has been traversed. In particular, the tip 32w may comprise at least two or more parts or petals that reposition to the side of the shaft 34w in the second, insufflating position. FIG. 14(c) illustrates the tip 32x in accordance with another aspect of the invention comprising a two-stage flip-top 290 that operates to move from a penetrating position to an insufflating position and then to an instrument access position. In particular, the two-stage flip-top 290 comprises a distal flip portion 292 and a proximal flip portion 294. In the first stage, the distal flip portion 292 moves from a penetrating position to an open or insufflating position once the body wall has been traversed. Once insufflation has been achieved, the proximal flip portion 294 moves to an open or instrument access position in the second stage. The tip 32x may further comprise retention members for connecting between the distal flip portion 292 and the proximal flip portion 294, and between the proximal flip portion 294 and the shaft 34x.

Figures 15A, 15B, 15C:
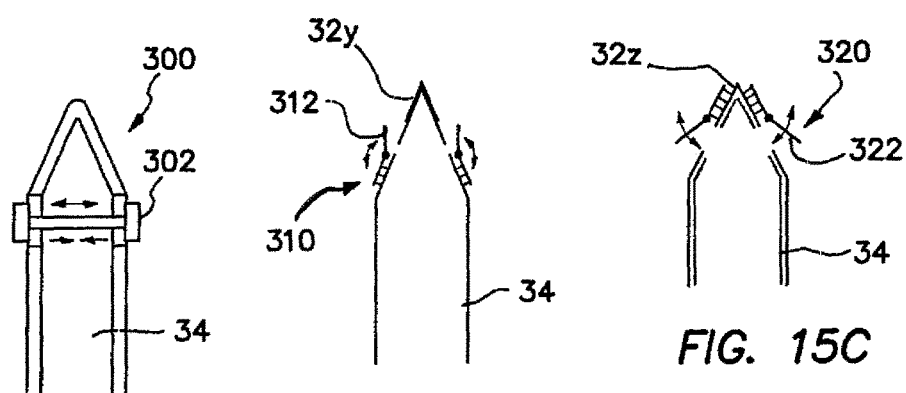
FIGS. 15(a)-15(c) illustrate cross-sectional views of insufflating valve vents in accordance with additional embodiments of the invention.

FIGS. 15(a)-15(c) illustrate insufflating valve vents in accordance with additional aspects of the invention. More specifically, FIG. 15(a) illustrates an insufflating valve vent 300 formed at the distal end of the shaft 34. The insufflating valve vent 300 is formed of an elastic material to allow gas such as $CO_2$ to be introduced from the inside of the shaft 34 to a body cavity. It is appreciated that when there is no gas, the elastic material of the insufflating valve vent 300 causes it to close so as to provide an airtight seal. FIG. 15(b) illustrates an insufflating flapper valve 310 formed at tip 32y of an insufflating optical trocar. The insufflating flapper valve 310 comprises at least one flapper valve vent 312 that operates to open when a gas such as $CO_2$ is introduced in the shaft 34. It is appreciated that when there is no gas, the flapper valve vent 312 closes to provide a tight seal. Similarly to FIG. 15(b), FIG. 15(c) illustrates an insufflating reverse flapper valve 320 formed at tip 32z of an insufflating optical trocar. The insufflating reverse flapper valve 320 comprises at least one flapper valve vent 322 that remains close or shut by tissue during insertion, and once peritoneum is passed, pressure by a gas such as $CO_2$ would then open the reverse flapper valve 320 to allow the transfer of the gas into a body cavity. It is appreciated that each of the above flapper valve vents may be spring loaded to operate like a Veress needle.

Figure 16:
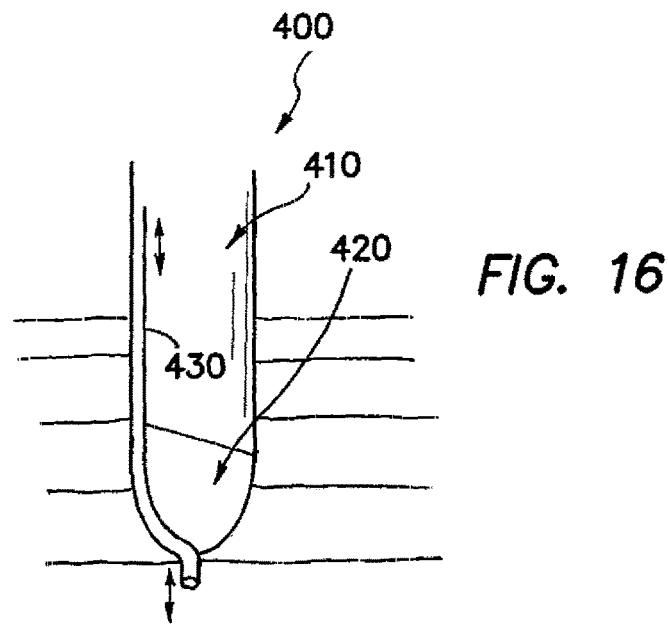
FIG. 16 illustrates a blunt tip insufflating optical instrument having an advanceable lumen in accordance with another embodiment of the invention.

FIG. 16 illustrates a blunt tip insufflating optical instrument 400 in accordance with another embodiment of the invention. The blunt tip insufflating optical instrument 400 comprises an elongate tubular body 410 extending along an axis between a proximal end and a distal end, a blunt tip optical obturator or separator 420 to be inserted through the tubular body 410 and into a body cavity, and an advanceable insufflation channel 430 extending along the length of the tubular body 410 and into the body cavity. The blunt tip optical obturator or separator 420 operates to provide visibility down to the peritoneum at which time the insufflation channel 430 may be advanced through the peritoneum to provide gas and/or saline to the body cavity until sufficient space is achieved. Once gas and/or saline have been sufficiently introduced, the blunt tip optical obturator 420 and tubular body 410 may be advanced into the body cavity. A feature of this aspect of the invention is the insufflation channel 430 may be advanced ahead of the blunt tip optical obturator or separator 420 to puncture peritoneum to transfer gas such as $CO_2$ to the body cavity.

Figure 17A:
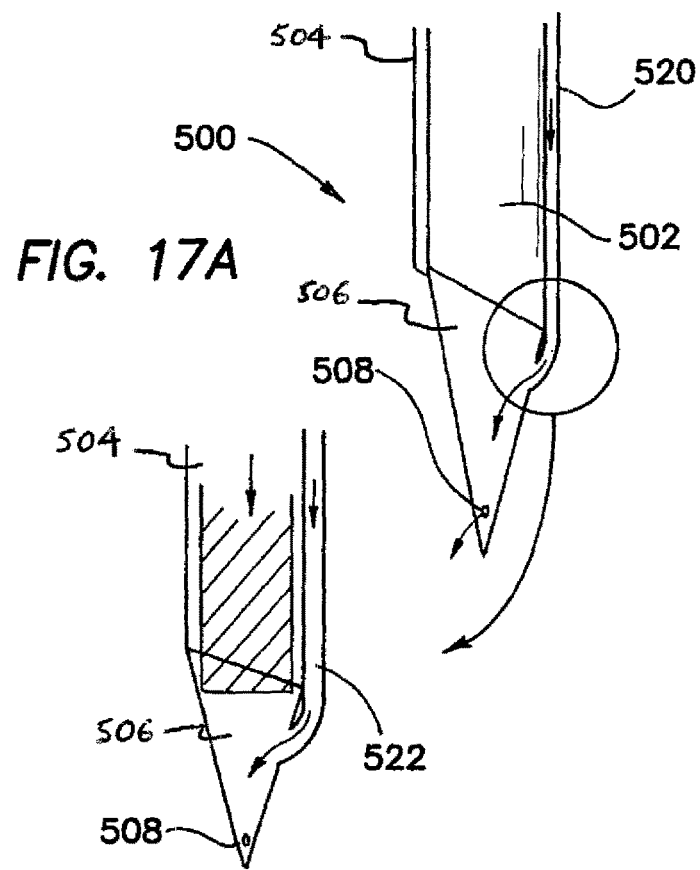
FIGS. 17(a) and 17(b) illustrate an insufflating surgical instrument including an insufflating optical trocar and a cannula having a gas channel for transferring insufflation gas to the trocar in accordance with another embodiment of the invention.
Figure 17B:
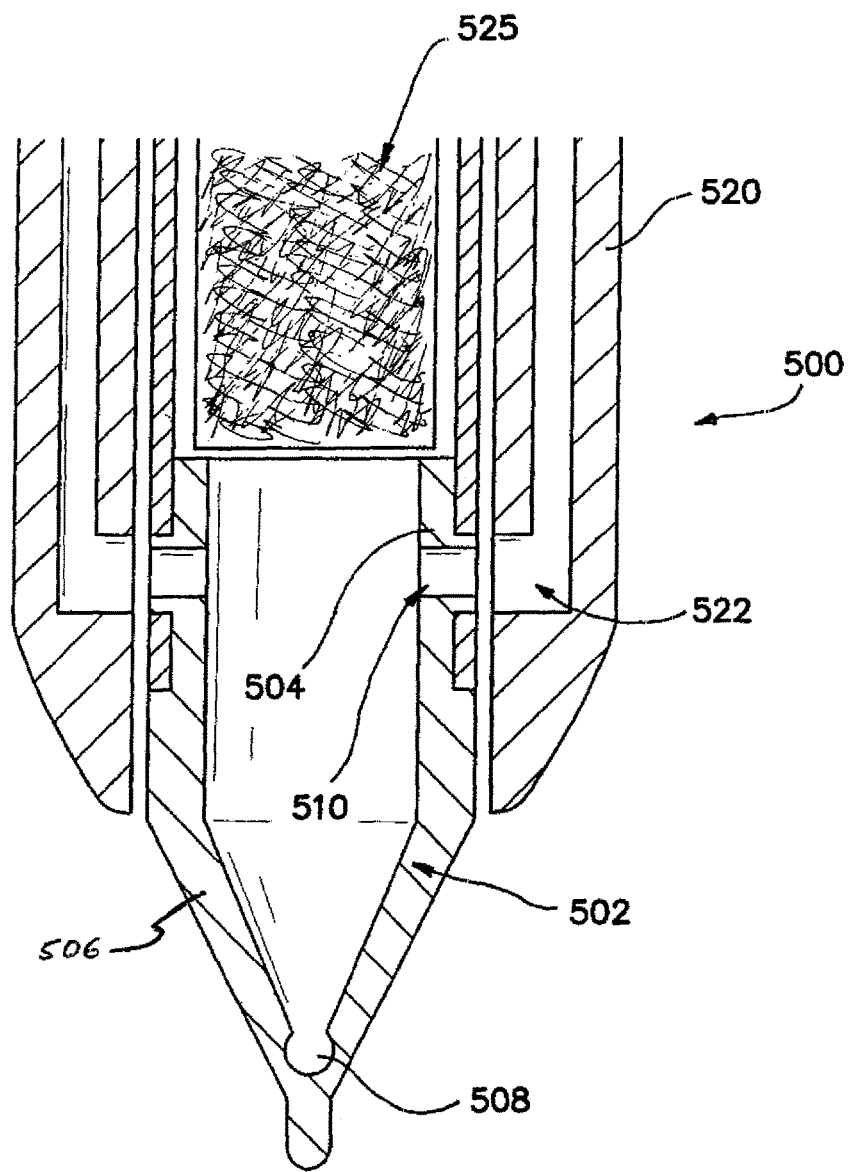

Referring to FIGS. 17(a) and 17(b), there are shown illustrations of an insufflating surgical instrument 500 in accordance with another embodiment of the invention. The insufflating surgical instrument 500 comprises an insufflating optical trocar 502 and a cannula 520. The insufflating optical trocar 502 comprises a shaft 504 having a lumen extending along an axis between a proximal end and a distal end, a tip 506 disposed at a distal end of the shaft, at least one vent hole 508 to introduce gas from the cannula 520 into the body or abdominal cavity as further discussed below, and a gas channel 510 formed in either the shaft 504 or the tip 506 and operably connected to the at least one vent hole 508 to allow gas transfer from the cannula 520 to the insufflating optical trocar 502. The cannula 520 comprises at least one cannula gas channel 522 extending along its longitudinal axis to transfer gas to the trocar gas channel 510 after insertion of the insufflating optical trocar 502 into the cannula 520. In other words, the cannula gas channel 522 is encased as a lumen in the cannula wall. During operation, the transfer of gas only takes place if there is an alignment between the cannula gas channel 522 and the trocar gas channel 510 as illustrated in FIGS. 17(*a*) and 17(*b*). A scope 525 may be inserted at the proximal end of the insufflating optical trocar 502 and then advanced to the distal end of the trocar 502 as the trocar 502 is placed through an abdominal wall.

Figure 18:
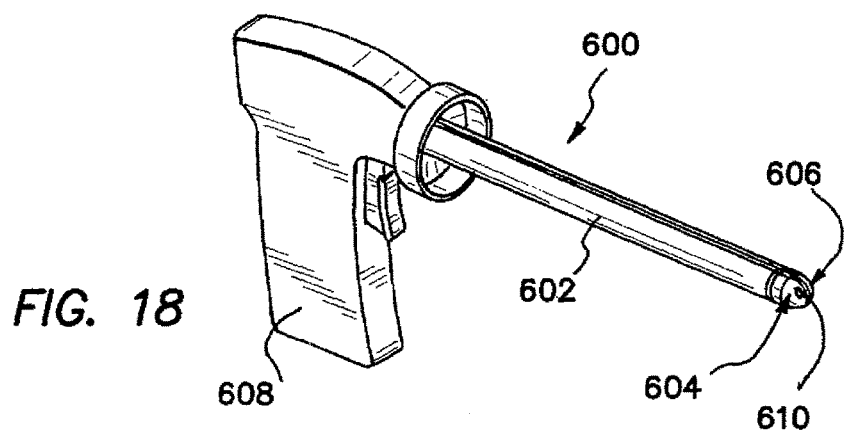
FIG. 18 illustrates an insufflating blade actuating optical trocar in accordance with another embodiment of the invention.

In yet another aspect of the invention, FIG. 18 illustrates an insufflating blade actuating optical instrument 600 in accordance with another embodiment of the invention. The insufflating blade actuating optical instrument 600 comprises an elongate tubular member 602 extending along a longitudinal axis between a proximal end and a distal end, an optical member 604 operably attached at the distal end of the elongate member 602, at least one blade member 606 being longitudinally movable between deployed and nondeployed positions, an actuating mechanism 608 operably attached at the proximal end of the tubular member 602 for moving the blade member 606 between the deployed and nondeployed positions, and at least one insufflating vent 610 formed in the optical member 604 to transfer insufflation gas from outside a body cavity to inside the body cavity. A scope may be inserted at the proximal end of the insufflating blade actuating optical instrument 600 and then advanced to the distal end of the instrument 600 as the insufflating blade actuating optical instrument 600 is placed through an abdominal wall.

Referring to FIGS. 19(*a*)-19(*i*), there are shown additional tip designs 32*aa*-32*ii* in accordance with other aspects of the invention to facilitate penetration of a body tissue. Each of these tip designs includes at least one vent hole (36*aa*-36*ii*) at the distal tip to introduce insufflation gas into a body cavity. It is appreciated that some of these tips have a sharp, pointed or bladed tip and/or edge to facilitate penetration of body tissue.

It is appreciated that the above described surgical instruments and devices can be used to access not only the peritoneal cavity but can be used for preperitoneal hernia repair, retroperitoneal operations including back and kidney operations, percutaneous kidney operations, thoracic surgery and arthroscopic access. In addition to gas such as carbon dioxide, it is appreciated that other fluids such as air, water and saline can also be introduced into a body cavity with the technique of the invention. It is appreciated that operating scopes may be modified such that a lumen may be used to introduce insufflation fluid. Accordingly, it is understood that many other modifications can be made to the various disclosed embodiments without departing from the spirit and scope of the invention. For these reasons, the above description should not be construed as limiting the invention, but should be interpreted as merely exemplary embodiments.

The invention claimed is:

1. An insufflating surgical instrument adapted for movement across an abdominal wall to insufflate an abdominal region of a patient comprising:
   a cannula having a wall forming a first lumen extending along an axis between a proximal end and a distal end of the cannula, and an insufflation channel extending along the axis between the proximal end and the distal end of the cannula and being adapted for connection to a source of fluid under pressure at the proximal end;
   a trocar insertable into and removable from the cannula, the trocar having a shaft with a second lumen extending along the axis between a proximal end and a distal end of the shaft, and a transparent tip at the distal end of the shaft enclosing the distal end of the shaft to prevent surgical instruments from extending through the distal end of the shaft; and at least one vent hole formed in the tip or at least one shaft vent formed along the shaft being in connection with the insufflation channel; wherein the shaft of the insufflating trocar has a diameter sized to enable insertion of a laparoscope; and
   a distal cannula seal positioned at the distal end of the cannula within the first lumen between the cannula and the trocar.

2. The insufflating surgical instrument of claim 1 further including the at least one vent hole formed at the tip being in connection with the insufflation channel and the at least one shaft vent being in connection with the insufflation channel and formed along the shaft.

3. The insufflating surgical instrument of claim 1 further including the at least one vent hole formed at the tip, the at least one vent hole being in connection with the insufflation channel and being adapted to expel the fluid under pressure to insufflate the abdominal region.

4. The insufflating surgical instrument of claim 1 wherein the shaft and the tip of the insufflating trocar have diameters sized to enable insertion of a laparoscope.

5. The insufflating surgical instrument of claim 1 wherein the first lumen and the insufflation channel are separated.

6. An insufflating surgical instrument adapted for movement across an abdominal wall to insufflate an abdominal region of a patient comprising:
   a cannula having a wall forming a first lumen extending along an axis between a proximal end and a distal end of the cannula, and an insufflation channel extending along the axis between the proximal end and the distal end of the cannula and being adapted for connection to a source of fluid under pressure at the proximal end;
   a trocar insertable into and removable from the cannula, the trocar having a shaft with a second lumen extending along the axis between a proximal end and a distal end of the shaft, and a transparent tip at the distal end of the shaft enclosing the distal end of the shaft to prevent surgical instruments from extending through the distal end of the shaft; wherein the tip is tapered and includes at least one vent hole formed in a tapered portion; wherein the shaft of the insufflating trocar has a diameter sized to enable insertion of a laparoscope; and
   a distal cannula seal positioned at the distal end of the cannula within the first lumen between the cannula and the trocar.

7. The insufflating surgical instrument of claim 6 wherein the insufflation channel is encased in the wall of the cannula.

8. An insufflating surgical instrument adapted for movement across an abdominal wall to insufflate an abdominal region of a patient comprising:
   a cannula having a wall forming a first lumen extending along an axis between a proximal end and a distal end of the cannula, and an insufflation channel extending along the axis between the proximal end and the distal end of the cannula and being adapted for connection to a source of fluid under pressure at the proximal end; the cannula further including a seal housing disposed at the proximal end of the cannula including a septum seal and a zero seal;

a trocar insertable into and removable from the cannula, the trocar having a shaft with a second lumen extending along the axis between a proximal end and a distal end of the shaft, and a transparent tip at the distal end of the shaft enclosing the distal end of the shaft to prevent surgical instruments from extending through the distal end of the shaft; wherein the shaft of the insufflating trocar has a diameter sized to enable insertion of a laparoscope; and a distal cannula seal positioned at the distal end of the cannula within the first lumen between the cannula and the trocar.

9. An insufflating surgical instrument adapted for movement across an abdominal wall to insufflate an abdominal region of a patient comprising:

a cannula having a wall forming a first lumen extending along an axis between a proximal end and a distal end of the cannula, and an insufflation channel extending along the axis between the proximal end and the distal end of the cannula and being adapted for connection to a source of fluid under pressure at the proximal end; wherein the first lumen and the insufflation channel are combined as one channel;

a trocar insertable into and removable from the cannula, the trocar having a shaft with a second lumen extending along the axis between a proximal end and a distal end of the shaft, and a transparent tip at the distal end of the shaft enclosing the distal end of the shaft to prevent surgical instruments from extending through the distal end of the shaft; wherein the shaft of the insufflating trocar has a diameter sized to enable insertion of a laparoscope; and a distal cannula seal positioned at the distal end of the cannula within the first lumen between the cannula and the trocar.

10. The insufflating surgical instrument of claim 9 further including a vent hole formed in the tip and in connection with the insufflation channel.

11. The insufflating surgical instrument of claim 9 further including at least one shaft vent formed in the shaft and in connection with the insufflation channel.

12. The insufflating surgical instrument of claim 9 wherein the tip is tapered.

13. An insufflating surgical instrument adapted for movement across an abdominal wall to insufflate an abdominal region of a patient comprising:

a cannula comprising a wall forming a first lumen and an insufflation channel extending along an axis between a proximal end and a distal end of the cannula and adapted for connection to a source of insufflation fluid under pressure at the proximal end of the cannula;

a trocar insertable into and removable from the first lumen of the cannula the trocar comprising a shaft having a wall forming a second lumen extending between a proximal end and a distal end of the shaft and a tip at the distal end of the shaft enclosing the distal end of the shaft; the shaft being configured to enable insertion of a laparoscope; wherein the tip is tapered and includes at least one vent hole formed in a tapered portion;

wherein at least one of the tip and the shaft is formed of a transparent material to facilitate visualization of the abdominal wall and the abdominal region; and wherein the shaft further comprises a scope stop configured to prevent the laparoscope from being inserted too far into the shaft and blocking the at least one of the insufflation channel and the vent hole.

14. The insufflating surgical instrument of claim 13 wherein the scope stop includes a ledge.

15. The insufflating surgical instrument of claim 13 wherein the tip at the distal end includes a taper of an inner diameter of the trocar and the scope stop is configured to keep the laparoscope from being inserted into the taper of the inner diameter of the trocar.

16. The insufflating surgical instrument of claim 13 wherein the shaft and the tip are configured to enable insertion of a laparoscope.

17. The insufflating surgical instrument of claim 13 further including a distal cannula seal positioned at the distal end of the cannula within the first lumen between the cannula and the trocar.

18. The insufflating surgical instrument of claim 13 wherein the first lumen and the insufflation channel are combined as one channel.

19. The insufflating surgical instrument of claim 13 wherein the at least one vent hole is in connection with the insufflation channel and further including at least one shaft vent being in connection with the insufflation channel and formed along the shaft.

* * * * *